(12) United States Patent
Sato et al.

(10) Patent No.: US 12,178,938 B2
(45) Date of Patent: Dec. 31, 2024

(54) UV ABSORBING OCULAR LENS

(71) Applicant: SEED CO., LTD., Tokyo (JP)

(72) Inventors: Takao Sato, Tokyo (JP); Yoshiko Yamazaki, Saitama (JP); Johan Sebastian Basuki, Australian Capital Territory (AU); Timothy Charles Hughes, Australian Capital Territory (AU); James Matthew MacDonald, Australian Capital Territory (AU); Kimmo Petteri Kemppinen, Australian Capital Territory (AU)

(73) Assignee: SEED CO., LTD., Tokyo (JP)

( * ) Notice: Subject to any disclaimer, the term of this patent is extended or adjusted under 35 U.S.C. 154(b) by 827 days.

(21) Appl. No.: 17/298,684

(22) PCT Filed: Dec. 10, 2019

(86) PCT No.: PCT/AU2019/051356
§ 371 (c)(1),
(2) Date: Jun. 1, 2021

(87) PCT Pub. No.: WO2020/118361
PCT Pub. Date: Jun. 18, 2020

(65) Prior Publication Data
US 2022/0040373 A1 Feb. 10, 2022

(30) Foreign Application Priority Data

Dec. 10, 2018 (AU) .................................. 2018904686

(51) Int. Cl.
*A61L 27/16* (2006.01)
*A61F 2/16* (2006.01)
(Continued)

(52) U.S. Cl.
CPC ............... *A61L 27/16* (2013.01); *A61F 2/16* (2013.01); *A61L 27/50* (2013.01); *C07C 323/60* (2013.01);
(Continued)

(58) Field of Classification Search
CPC .... C08F 220/20; C08F 220/06; C08F 220/68; C08F 220/606; C08F 222/103;
(Continued)

(56) References Cited

U.S. PATENT DOCUMENTS 4,963,160 A  10/1990  Jung et al.
5,637,726 A   6/1997  Collins et al.
(Continued)

FOREIGN PATENT DOCUMENTS

CN    103374097    10/2013
CN    107176931     9/2017
(Continued)

OTHER PUBLICATIONS

Office Action from JPO (English machine translation of Office Action), Patent Application No. JP2021-527059 Date of Drafting: Sep. 26, 2023.
(Continued)

*Primary Examiner* — Peter A Salamon
(74) *Attorney, Agent, or Firm* — JMB Davis Ben-David

(57) ABSTRACT

Ocular lenses having UV absorbing properties are disclosed. The ocular lens comprises a hydrogel polymer comprising polymerised residues derived from a polymerisable UV absorber of formula (I):

$$U\text{-}L\text{-}Py \qquad (I)$$

wherein: U is a UV absorbing moiety; L is a hydrophilic non-polyalkylene glycol linker comprising an anionic, a
(Continued)

zwitterionic or a saccharide moiety; and Py is an ethylenically unsaturated polymerisable moiety.

18 Claims, 10 Drawing Sheets

(51) Int. Cl.
    *A61L 2/16*     (2006.01)
    *A61L 27/20*     (2006.01)
    *A61L 27/50*     (2006.01)
    *C07C 323/60*     (2006.01)
    *C07D 249/20*     (2006.01)
    *C07F 9/09*     (2006.01)
    *C07H 15/26*     (2006.01)
    *G02B 1/04*     (2006.01)

(52) U.S. Cl.
    CPC ............ *C07D 249/20* (2013.01); *C07F 9/091* (2013.01); *C07H 15/26* (2013.01); *G02B 1/043* (2013.01); *A61F 2002/16965* (2015.04); *A61L 2430/16* (2013.01)

(58) Field of Classification Search
    CPC .............. C08F 222/245; C08F 220/387; C08F 222/38; C08F 220/36; G02B 1/043; C08L 2666/70; C08L 35/02; C08L 33/14
    See application file for complete search history.

(56) References Cited

U.S. PATENT DOCUMENTS

| | | | |
|---|---|---|---|
| 7,803,359 B1 | 9/2010 | Jinkerson et al. | |
| 7,915,322 B2* | 3/2011 | Hung | C08F 220/26 |
| | | | 523/108 |
| 8,043,607 B2* | 10/2011 | Jinkerson | C07D 249/20 |
| | | | 351/159.63 |
| 2001/0025198 A1 | 9/2001 | Faubl | |
| 2007/0082019 A1 | 4/2007 | Huang | |
| 2010/0120939 A1* | 5/2010 | Phelan | C08F 230/08 |
| | | | 564/169 |
| 2011/0063567 A1* | 3/2011 | Domschke | C08G 77/388 |
| | | | 525/100 |
| 2013/0095235 A1* | 4/2013 | Bothe | B29D 11/00125 |
| | | | 427/160 |
| 2017/0158611 A1* | 6/2017 | Chang | C07D 249/20 |
| 2017/0242274 A1* | 8/2017 | Holland | C07C 237/34 |
| 2017/0242275 A1* | 8/2017 | Chang | B29D 11/00134 |
| 2018/0043066 A1* | 2/2018 | Grinstaff | A61L 31/10 |
| 2018/0141293 A1* | 5/2018 | Bothe | B29D 11/00038 |
| 2019/0002415 A1 | 1/2019 | Mahadevan et al. | |

FOREIGN PATENT DOCUMENTS

| | | |
|---|---|---|
| EP | 1077952 | 2/2001 |
| JP | 11292938 | 10/1999 |
| JP | 2016-109830 | 6/2016 |
| WO | 9958507 | 11/1999 |
| WO | 2006096422 | 9/2006 |
| WO | 2008134674 | 11/2008 |
| WO | 2009021097 | 2/2009 |
| WO | 2010078001 | 7/2010 |
| WO | 2013177506 | 11/2013 |
| WO | 2015164582 | 10/2015 |
| WO | 2016048853 | 3/2016 |
| WO | 2019/002971 | 1/2019 |

OTHER PUBLICATIONS

Written Opinion from Intellectual Property Office of Sigapore—Patent Application No. SG 11202106187U; Date of Drafting: Sep. 19, 2022.
Notification concerning transmittal of international preliminary report on patentability (Form PCT/IB/326) for International Patent App. No. PCT/AU2019/051356.
International preliminary report on patentability (Form PCT/IB/373)for International Patent App. No. PCT/AU2019/051356.
International-type Search report Patent Application No. AU2018904686 (Date of Drafting: May 30, 2019).
Chinese Office action (Including English machine translation of Office Action) Patent Application No. 201980081375.6 Date of Drafting: Feb. 26, 2024.
Extended European Search Report of corresponding EP Patent Application No. 19895596.5.

* cited by examiner derground # UV ABSORBING OCULAR LENS

CROSS-REFERENCE TO RELATED APPLICATIONS

This is the U.S. National Stage of International Patent Application No. PCT/AU2019/051356 filed on Dec. 10, 2019, which in turn claims the benefit of Australian Patent Application No. 2018904686 filed on Dec. 10, 2018.

TECHNICAL FIELD

The present invention relates to a UV absorbing ocular lens. In particular, the invention relates to UV absorbing ocular lenses comprising hydrogel polymers formed with a polymerisable hydrophilic non-polyalkylene glycol UV absorber that is capable of blocking UV radiation.

BACKGROUND

Ocular lenses such as contact lenses and intraocular lenses are ophthalmic devices that are placed in or on the eye to address particular vision defects.

Specifically, contact lenses are thin shaped films that are placed on the cornea to correct vision. Contact lenses can be made of hard or soft materials, with the latter form being the more popular choice. Improvements in the comfort (i.e. softness, wettability) and safety (i.e. increased oxygen permeability) of contact lenses have led to their increased adoption over spectacles. Intraocular lenses (IOLs) are artificial lens replacements designed for implantation inside the eye to replace the eye's natural lens when it is removed during cataract surgery.

Contact lenses can be broadly classified by their water content and their degree of oxygen permeability. The first contact lenses developed, which are still available, were (meth)acrylate-based hydrogel type lenses. Those lenses generally have low oxygen permeable lenses and are either rigid or soft in form. The rigid lenses have a relatively low water content and maintain their own shape unsupported and are made of transparent optical grade polymers, such as polymethylmethacrylate (PMMA) or cellulose acetate butyrate (CAB). The soft lenses are typically more hydrophilic, have a higher water content and can be fabricated using hydrophilic monomers such as 2-hydroxyethyl methacrylate (HEMA).

Silicone based hydrogel lenses were developed in the 1990s. Those lenses typically exhibit high oxygen permeability and low water content. Silicone based hydrogel lenses can include polysiloxanes (silicone resins), fluoropolymers, and fluorosiloxanes. As silicone hydrogels allow increased oxygenation to the cornea, they permit safe, overnight wear and have largely eliminated hypoxia, whether worn on a daily or overnight basis. Currently, silicone based hydrogel lenses account for more than half of all prescribed lenses.

While silicone hydrogels can offer greater oxygen permeability, they are generally more hydrophobic than their non-silicone hydrogel counterparts due to the incorporation of various siloxane components. As such, there are still reports of unexpected discomfort and dryness and in some cases, heavy surface deposits, contact lens-induced papillary conjunctivitis (CLPC), conjunctival inflammation and corneal staining as a result of exposure to silicone. Nevertheless, among wearers of daily disposable lenses, both HEMA hydrogel and silicone hydrogel based contact lenses are still in demand. Hydrogel-based lenses also continue to be useful as intraocular lenses as a result of their greater stability compared to silicone based lenses.

Ocular lenses providing some protection to the eye against UV light have been developed in response to increased awareness of the harm caused by UV rays. Both acute and chronic UV exposure can lead to damage to the cornea and diseases such as cataracts, photokeratitis and age-related macular degeneration (AMD). UV absorbers initially incorporated in ocular lenses were compounds used for decades in stabilising comodity polymers against the degrading effects of UV radiation. Such compounds were typically incorporated in the lenses simply by blending them with the base polymer.

Some well-known UV absorbing compounds used in contact lenses belong to classes such as benzotriazoles, benzophenones and triazines. Each class has its own UV absorbance characteristics. For example, benzophenone and triazine types tend to absorb more strongly in the short wavelength UV-B region than the benzotriazole types. 2-[3-(2H-benzotriazol-2-yl)-4-hydroxyphenyl]ethyl methacrylate or HB7 (CAS: 96478-09-0) is widely used as a polymerisable UV absorber in the contact lens industry.

However, a problem with application of UV absorbers that are merely blended with the base polymer is the absorber can leach out of the polymer during use. Polymerisable UV absorbers that can be covalently bonded to the base polymer are therefore often preferred.

A number of polymerisable UV absorbing compounds have been described. For example, a new class of styrenic benzotriazoles is described in U.S. Pat. No. 5,637,726 as being useful in soft contact lenses. Other derivatives of benzotriazole type UV absorbers containing polymerisable groups are also described in JP2002521705, WO2006/096422, U.S. Pat. Nos. 7,915,322, 7,803,359, 8,043,607, CN103374097 and EP1077952. For example WO2006/096422 describes the preparation of a high-molecular weight hydrophilic polymer with a 2-[3'-t-butyl-5'-(methacryloxypropyl)-2'-hydroxyphenyl]-5-chloro benzotriazole UV absorbing monomer.

Contact lenses comprising UV absorbers can be classified as Class I or Class II lenses according the level of UV protection they afford. The American National Standard Institute (ANSI) classifies contact lenses blocking 90% of UVR-A and 99% of UVR-B as Class I, while contact lenses blocking 70% of UVR-A and 95% of UVR-B are classified as Class II. The International Standards Organization (ISO) classifies contact lenses blocking >90% of UVR-A and >99% of UVR-B as Class I, while contact lenses blocking >50% of UVR-A and >95% of UVR-B are classified as Class II.

However, there are some challenges in making Class I and Class II hydrogel-based contact lenses. One issue is that a number of UV absorbers are hydrophobic. They can thus have limited compatibility with hydrogel-forming monomers, which can make it difficult to synthesise UV absorbing hydrogel ocular lenses meeting a selected UV blocking standard. Use of UV absorbers in hydrogel polymers can also compromise properties such as the water content and optical transparency of the hydrogel. In some instances, the UV absorbers may also adversely affect the durability and flexibility of the hydrogel and its stability to sterilizing regimes. Moreover, when a benzotriazole is used, high concentrations of the UV absorbing compound may be required for the lens to meet a target UV blocking standard. That in turn can lead to the lens absorbing significant amounts of light at the upper end of the UVA range and into the visible light range, resulting in an undesirable yellowish tint in the lens. If high quantities of UV absorbers are used in lenses, it can also lead to a risk of excess UV absorbing compounds leaching out into the eye during use.

Hung et al., in U.S. Pat. No. 4,963,160, proposed a solution to some of those problems by incorporating two different UV absorbing components with different UV absorbing spectra onto a triazine derivative, which is then applied as a coating onto a polymeric contact lens.

UV absorbing agents including a combination of UV absorbing compounds, such as p-aminobenzoic acid and a benzotriazole or p-aminobenzoic acid and a benzophenone, have also been described in the prior literature. However, the use of those UV absorbing agents with ocular lenses have certain limitations because the UV absorbing compounds can only be used in a one-to-one (1:1) mole ratio, so that the UV absorption spectra of the lens cannot be optimized.

WO2009/021097 describes a novel UV absorber for use in silicone containing contact lens particularly useful in intraocular lens that purports to have the ability to absorb both UV and blue light, a useful characteristic in IOLs.

A monomer bearing a UV absorbing moiety linked to a polymerisable group such as methacrylate via a polyethylene glycol (PEG) linker for inclusion in hydrogel materials has been described in CN 103374097. However, the water content and UV blocking performance of hydrogel-containing lenses formed with the PEG containing UV absorbing monomer can be below acceptable industry standards in some instances.

The present invention seeks to ameliorate or overcome one or more problems of the prior art and to provide a UV absorbing hydrogel-containing ocular lens that can effectively absorb UV radiation while at least meeting acceptable specifications for the hydrogel material.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY

The present invention relates generally to UV absorbing ocular lenses for use on or in the eye. The invention seeks to provide hydrogel-containing ocular lenses that have effective UV blocking capability while retaining acceptable characteristics for the hydrogel material.

In a first aspect, the present invention provides an ocular lens comprising a hydrogel polymer comprising polymerised residues derived from a polymerisable UV absorber of formula (I):

U-L-Py    (I)

wherein:
U is a UV absorbing moiety;
L is a hydrophilic non-polyalkylene glycol linker comprising an anionic, a zwitterionic or a saccharide moiety; and
Py is an ethylenically unsaturated polymerisable moiety.

In one embodiment of an ocular lens according to the first aspect, the hydrophilic non-polyalkylene glycol linker (L) comprises at least 4 carbon atoms.

In one embodiment of an ocular lens according to the first aspect, the hydrophilic non-polyalkylene glycol linker (L) comprises a moiety selected from carboxylate, sulfonate, sulfate, phosphate, phosphonate, ammonium, and combinations thereof.

In one embodiment of an ocular lens according to the first aspect, the hydrophilic non-polyalkylene glycol linker (L) comprises a moiety selected from formula (IIa), (IIb), (IIc), (IId), and (IIe):

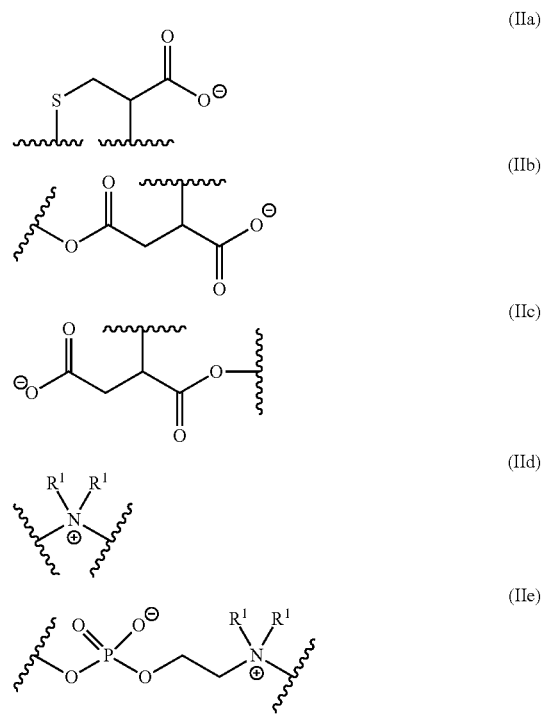

wherein $R^1$ at each occurrence is independently selected from H and $C_1$-$C_4$ alkyl (preferably methyl), and  represents the remainder of the polymerisable UV absorber of formula (I).

In one embodiment of an ocular lens according to the first aspect, the hydrophilic non-polyalkylene glycol linker (L) has a structure selected from formula (IIIa), (IIIb), (IIIc) and (IIId):

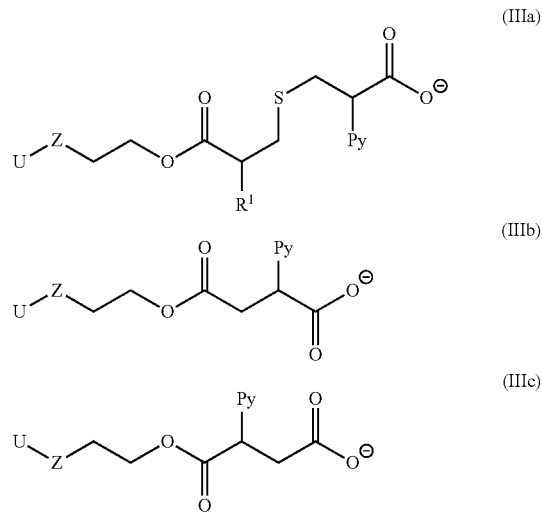

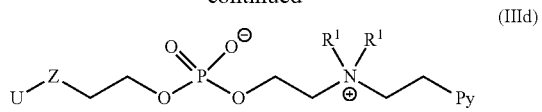

(IIId)

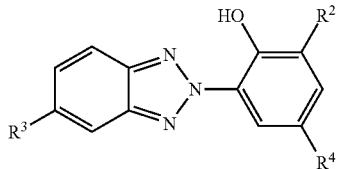

(IV)

wherein:
- $R^1$ at each occurrence is independently selected from H and $C_1$-$C_4$ alkyl (preferably methyl);
- Z is absent or is a heteroatom (preferably O);
- U is the UV absorbing moiety; and
- Py is the ethylenically unsaturated polymerisable moiety.

In another embodiment of an ocular lens according to the first aspect, the hydrophilic non-polyalkylene glycol linker (L) comprises a saccharide moiety. The saccharide moiety may be in cyclic or acyclic form. In one embodiment, L comprises a cyclic saccharide moiety selected from a furanose, pyranose and amino sugar moiety. In a particular embodiment, the hydrophilic non-polyalkylene glycol linker (L) comprises a glucopyranose or glucosamine moiety.

In one embodiment of an ocular lens according to the first aspect, the hydrophilic non-polyalkylene glycol linker (L) has a structure selected from formula (Xa) and (Xb):

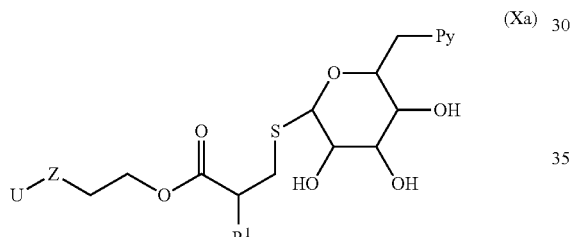

(Xa)

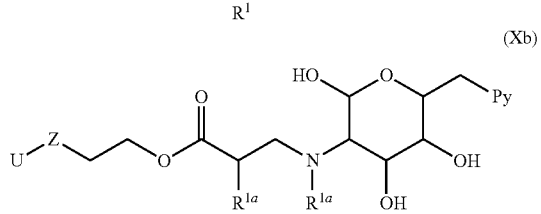

(Xb)

wherein in formula (Xa) and (Xb):
- $R^{1a}$ at each occurrence is independently selected from H and $C_1$-$C_4$ alkyl;
- Z is absent or is a heteroatom (preferably O);
- U is the UV absorbing moiety; and
- Py is the ethylenically unsaturated polymerisable moiety.

In embodiments of an ocular lens according to the first aspect, the UV absorbing moiety of the polymerisable UV absorber is capable of absorbing radiation in the UV-A and/or UV-B range.

In some particular embodiments of the ocular lens of the first aspect, the UV absorbing moiety (U) of the polymerisable UV absorber is a benzotriazole or benzophenone moiety.

In one embodiment of an ocular lens according to the first aspect, the UV absorbing moiety (U) of the polymerisable UV absorber has a structure of formula (IV):

wherein
- $R^2$ is selected from H and $C_1$-$C_5$ alkyl;
- $R^3$ or $R^4$ represent an attachment point to the linker (L), and wherein:
  - if $R^3$ is the attachment point to the linker (L), then $R^4$ is selected from H, alkyl and alkoxy; and
  - if $R^4$ is the attachment point to the linker (L), then $R^3$ is selected from H, halo (preferably chloro) and $CF_3$.

In another embodiment of an ocular lens according to the first aspect, the UV absorbing moiety (U) of the polymerisable UV absorber has a structure of formula (V):

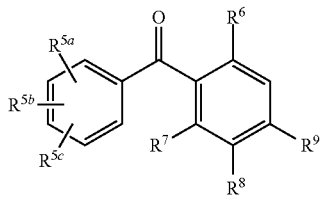

(V)

wherein
- $R^{5a}$, $R^{5b}$ and $R^{5c}$ are each independently selected from H, halo, hydroxyl, carboxylate, sulfonate, $C_1$-$C_6$ alkyl, $C_1$-$C_6$ alkoxy, $C_6$-$C_{10}$ aryl, and substituted aryl groups;
- $R^6$ and $R^7$ are each independently selected from H and OH with the proviso that $R^6$ and $R^7$ are not identical;
- $R^8$ is selected from H and sulfonate; and
- $R^9$ is the attachment point to the linker (L).

In some embodiments of an ocular lens according to the first aspect, the polymerisable UV absorber comprises an ethylenically unsaturated polymerisable moiety selected from allyl, vinyl, acryloyl, methacryloyl, and styrenyl.

In some embodiments of an ocular lens according to the first aspect, the hydrogel polymer comprises polymerised residues derived from at least two different polymerisable UV absorbers, wherein at least one of the polymerisable UV absorbers is of formula (I).

In some embodiments of an ocular lens according to the first aspect, the hydrogel polymer comprises from about 1.0 to about 10 wt % of polymerised residues derived from two or more polymerisable UV absorbers, based on the total weight of monomeric units in the polymer, wherein at least one of the UV absorbers is a polymerisable UV absorber of formula (I).

In some embodiments of an ocular lens according to the first aspect, the hydrogel polymer comprises polymerised residues derived from at least one ethylenically unsaturated monomer selected from acryloyl monomers, methacryloyl monomers, and combinations thereof.

In some embodiments of an ocular lens according to the first aspect, the hydrogel polymer comprises polymerised residues derived from an ethylenically unsaturated cross-linking agent.

An ocular lens according to the present invention can be a contact lens or an intraocular lens.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

BRIEF DESCRIPTION OF THE FIGURES

Embodiments of the invention will now be described with reference to the following non-limiting drawings in which.

DETAILED DESCRIPTION

Figure 1:
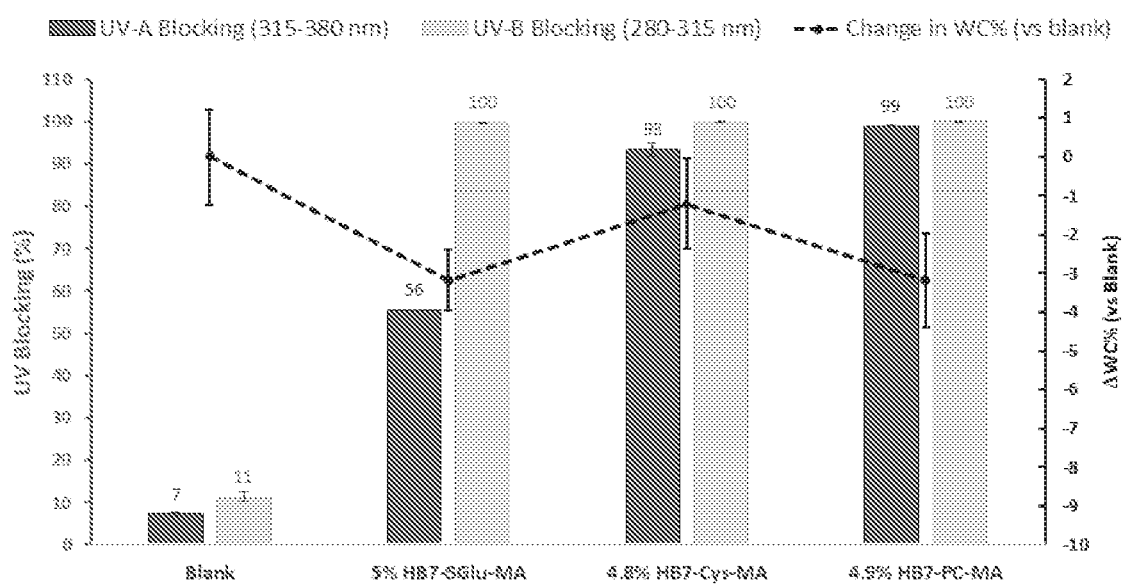
FIG. 1 is a graph illustrating the UV blocking performance and change in water content ($\Delta$WC % relative to the blank) results of hydrogel samples formed with polymerisable UV absorbers having a linker comprising a saccharide, anionic, or zwitterionic moiety and a hydroxyphenyl-benzotriazole UV absorbing moiety, compared to a blank hydrogel sample with no UV absorber.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

All percentages (%) referred to herein are percentages by weight (w/w or w/v), unless otherwise indicated.

Polymer molecular weights referred to herein are number average molecular weight ($M_n$), unless otherwise indicated.

As used herein, the term "hydrophilic" is meant that a compound, molecule, group or moiety has an affinity for water and is thus compatible with an aqueous medium and may be soluble in the aqueous medium. A preferred aqueous medium may be an aqueous solvent (such as water or a solvent containing water) or an aqueous solution (such as a buffer salt solution). In some embodiments, a hydrophilic compound, molecule, group or moiety may have a solubility in water of at least 10 g of per 100 g of water at 25° C.

The present invention relates generally to UV absorbing ocular lenses for use on or in the eye, and seeks to provide hydrogel-containing ocular lenses that have effective UV blocking capability while retaining acceptable characteristics for the hydrogel material.

Ocular lenses contemplated in connection with the present invention are ophthalmic devices intended for placement on or in an eye of a subject. Examples of ocular lenses include contact lenses, intraocular lenses and the like.

In one aspect, the present invention provides an ocular lens comprising a hydrogel polymer comprising polymerised residues derived from a polymerisable UV absorber of formula (I):

$$U\text{-}L\text{-}Py \qquad \qquad (I)$$

wherein:
U is a UV absorbing moiety;
L is a hydrophilic non-polyalkylene glycol linker comprising an anionic, a zwitterionic or a saccharide moiety; and
Py is an ethylenically unsaturated polymerisable moiety.

It has now been found UV absorbers of formula (I) can be polymerised to afford hydrogels that exhibit advatageous properties for use in ocular lens applications. In particular, ocular lenses comprising hydrogels derived from such UV absorbers have surprisingly and avatageously been found to exhibit high water content/retention and UV absorbing properties. Without wishing to be limited by theory, it is believed the form of the linker (L) plays an important role to achieving such properties.

Hydrogels are known as a class of polymer defined by an ability to be swollen by and to retain aqueous liquid within their polymer matrix. In their swollen state the polymer presents as a gel having a three-dimensional network of polymer chains that are typically crosslinked to prevent them from dissolving in the aqueous liquid. The hydrogel can contain an interpenetrating network of more than one polymer, such as hydrophilic polymer and silicone polymer, to provide a silicone hydrogel. Due to their aqueous liquid content, hydrogels are typically compatible with biological environments and can be used in the manufacture of ocular lenses, such as contact lenses and intraocular lenses, which are intended to be placed on or in an eye of a subject.

For convenience, the network polymer component of the hydrogel may also be referred to herein as a "hydrogel polymer".

Hydrogel polymer can be prepared by polymerising an effective amount of a polymerisable UV absorber of formula (I) with at least one suitable co-monomer. This results in covalent incorporation of the polymerisable UV absorber of formula (I) as polymerised residues in the polymer, together with the at least one co-monomer.

Incorporation of the co-monomer and the UV absorber of formula (I) as polymerised residues in the hydrogel polymer enable an ocular lens having effective UV absorption capability to be prepared.

The hydrogel polymer described herein comprises polymerised residues derived from at least one polymerisable UV absorber of formula (I). The UV absorber of formula (I) may be used either alone or in combination with at least one other polymerisable UV absorber, to impart UV absorbing properties to the ocular lens. Other polymerisable UV absorbers that can be used in combination with the UV absorber of formula (I) are described herein.

The polymerisable UV absorber of formula (I) is a monomer bearing a UV absorbing moiety that is attached to the ethylenically unsaturated polymerisable moiety via a hydrophilic non-polyalkylene glycol linker (L).

By the linker (L) of formula (I) being a "non-polyalkylene glycol linker" is meant that it does not comprise a moiety derived from or composed of a polyalkylene glycol (such as a $C_2$-$C_4$-polyalkylene glycol, for example polyethylene glycol or polypropylene glycol). For example, the non-polyalkylene linker does not comprise a moiety having a structure of —$(C_2H_4O)_n$—, —$(CH(CH_3)CH_2O)_n$— or —$(CH_2CH(CH_3)O)_n$—, where n is an integer in the range of from 2 to 10.

The hydrophilic non-polyalkylene glycol linker (L) is positioned in between the UV absorbing moiety (U) and the ethylenically unsaturated polymerisable moiety (Py) of the UV absorber and acts to covalently link the UV absorbing moiety and the ethylenically unsaturated polymerisable moiety to one another.

It is important the non-polyalkylene glycol linker (L) in the UV absorber of formula (I) be hydrophilic. It is believed the presence of a hydrophilic linker can help to improve the compatability of the UV absorber, as well as polymer materials containing the UV absorber, with an aqueous environment. Commonly used UV absorbers are hydrophobic, so the introduction of a hydrophilic non-polyalkylene glycol linker imparts a hydrophilic character to the hydrogel, such that desirable properties of the base hydrogel, including optical transparency and water content, are not unacceptably changed as a result of the incorporation of the UV absorber in the hydrogel polymer. The hydrophilic characteristic also helps to ensure that the polymerisable UV absorber is sufficiently compatible with other components used to form the hydrogel.

In some embodiments, the hydrophilicity of a non-polyalkylene glycol linker may be determined by assessing the solubility of a UV absorber containing the non-polyalkylene glycol linker in an aqueous liquid, such as water or a solution containing water (e.g. an aqueous monomer solution). For example, it has been found that in some instances, a greater quantity of a UV absorber of formula (I) can be dissolved in an aqueous liquid, compared to that of commercially available UV absorbers, such as 2-[3-(2H-benzotriazol-2-yl)-4-hydroxyphenyl]ethyl methacrylate (HB-7) and 2-(4-benzoyl-3-hydroxyphenoxy)ethyl acrylate (BP15), which do not have a hydrophilic linker and are generally considered to be hydrophobic. The ability to solubilise higher quantities of the UV absorber of formula (I) in an aqueous liquid is an indicator that the linker moiety of the UV absorber is hydrophilic and is able to influence the hydrophilicity of the molecule.

The polymer component of the hydrogel comprises polymerised residues of a polymerisable UV absorber of formula (I) in which L is a hydrophilic non-polyalkylene glycol linker (L) comprising an anionic, a zwitterionic or a saccharide moiety.

Without wishing to be limited by theory, it is believed use of such a linker (L) is advantageous in promoting electrostatic interactions with other components of the hydrogel (such as salts in the aqueous liquid component of the hydrogel) or the ocular lens. That in turn is believed to help the resultant hydrogel attract and/or retain water and in turn enhance the compatibility of the hydrogel material with the ocular environment.

Those skilled in the art will appreciate an anionic moiety will present a negative charge and a zwitterionic moiety will present both negative and positive charges.

Reference herein to "positive" or "negative" charge in a moiety of the non-polyalkylene linker is intended to mean that the moiety contains a functional group with a positive or negative charge, respectively. The functional group may of course initially be in a neutral state and subsequently be converted into its charged state. Thus, a charged moiety may inherently bear charge, or it may be capable of being converted into a charged state, for example through addition or removal of an electrophile.

In the case of a positive charge, the functional group may have an inherent charge, such as a quaternary ammonium functional group or moiety, or the functional group per se may be neutral, yet be chargeable to form a cation through, for example, pH dependent formation of a tertiary ammonium cation, or quaternerisation of a tertiary amine group.

In the case of negative charge, the functional group may, for example, comprise an organic acid salt that provides for the negative charge, or the functional group may comprise an acidic moiety which may be neutral, yet be chargeable to form an anion through, for example, pH dependent removal of an acidic proton.

In one set of embodiments, the hydrophilic non-polyalkylene glycol linker (L) comprises a charged moiety selected from carboxylate, sulfonate, sulfate, phosphate, phosphonate, and ammonium, and combinations thereof. The charged moiety may and in some embodiments preferably will be part of a larger charged group in the hydrophilic linker structure.

In one set of embodiments, the hydrophilic non-polyalkylene glycol linker (L) comprises an anionic moiety. Such anionic moieties may be selected form carboxylate, sulfonate, sulfate, phosphate and phosphonate moieties.

In another set of embodiments, the hydrophilic non-polyalkylene glycol linker (L) comprises a zwitterionic moiety. Zwitterionic moieties bear both a negative and positive charge, such as a cationic ammonium moiety in combination with an anionic carboxylate, sulfonate, sulfate, phosphate or phosphonate moiety. Exemplary zwitterionic moieties can be carboxybetaine, sulfobetaine and phosphorylcholine moieties.

In one set of embodiments, the hydrophilic non-polyalkylene glycol linker (L) comprises at least 4 carbon atoms. In some embodiments, the non-polyalkylene glycol linker comprises at least 5, at least 6, or at least 7 carbon atoms. The linker can preferably be an aliphatic moiety, which may be linear or cyclic. In some embodiments there may be one or more heteroatoms forming part of the structure of the non-polyalkylene glycol linker. Examples of heteroatoms include nitrogen (N), oxygen (O) and sulphur (S) heteroatoms. Without wishing to be limited by theory, providing the linker (L) with at least 4 carbon atoms is believed to minimize adverse interference between the linker with the UV absorbing moiety. By providing the linker with at least 4 carbon atoms it has been found the UV absorbing properties of the UV absorbing moiety can be maximised.

In some embodiments, the hydrophilic non-polyalkylene glycol linker (L) of the polymerisable UV absorber of formula (I) comprises a charged moiety selected from formula (IIa), (IIb), (IIe), (IId), and (IIe):

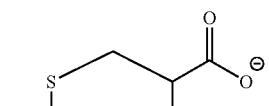

(IIa)

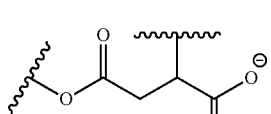

(IIb)

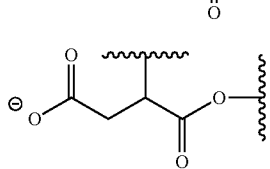

(IIc)

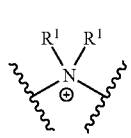

(IId)

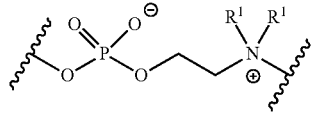

(IIe)

The hydrophilic non-polyalkylene glycol linker (L) of the polymerisable UV absorber of formula (I) may also comprises a charged moiety selected from formula (IIf), (IIg), (IIh) and (IIi):

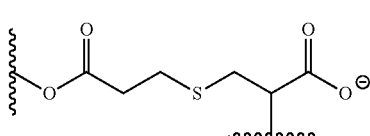

(IIf)

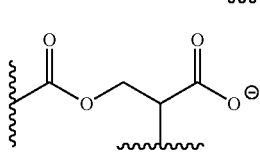

(IIg)

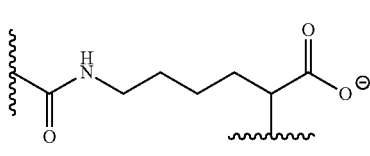

(IIh)

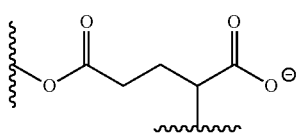

(IIi)

Specifically, in (IId) and (IIe) of the above formulae, $R^1$ at each occurrence is independently selected from H and $C_1$-$C_4$ alkyl. A preferred $C_1$-$C_4$ alkyl is methyl. The ∼∼∼ represents the remainder of the polymerisable UV absorber of formula (I).

Charged moieties such as those shown in formulae (IIa), (IIb), (IIc), (IId), (IIe), (IIf), (IIg), (IIh) and (IIi) may be derived from suitable precursor compounds, such as amino acids, amines (including primary, secondary or tertiary amines) and cyclic phosphate compounds.

In some embodiments, the charged moiety may be derived from an amino acid. Exemplary amino acids may be cysteine, aspartic acid and lysine. Amino acids may be useful for forming charged moieties of formulae (IIa), (IIb) and (IIc).

In particular embodiments of the ocular lens of the invention, the hydrogel may have a polymer component comprising polymerised residues of a polymerisable UV absorber comprising a hydrophilic non-polyalkylene glycol linker having a structure selected from formulae (IIIa), (IIIb), (IIIc), and (IIId):

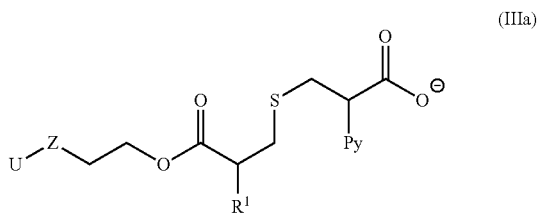

(IIIa)

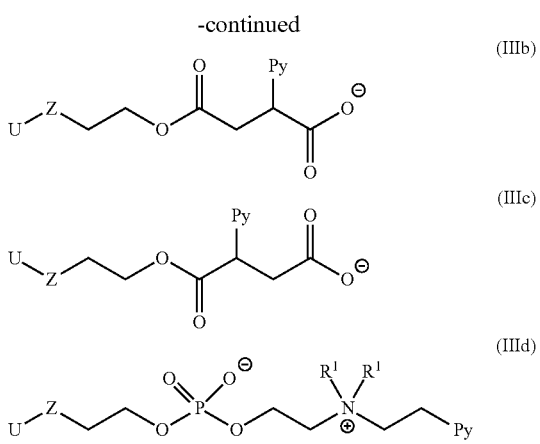

wherein:
R$^1$ at each occurrence is independently selected from H and C$_1$-C$_4$ alkyl;
Z is absent or is a heteroatom;
U is the UV absorbing moiety; and
Py is the ethylenically unsaturated polymerisable moiety.

The hydrogel may also have a polymer component comprising polymerised residues of a polymerisable UV absorber comprising a hydrophilic non-polyalkylene glycol linker having a structure selected from formulae (IIIe), (IIIf), and (IIIg):

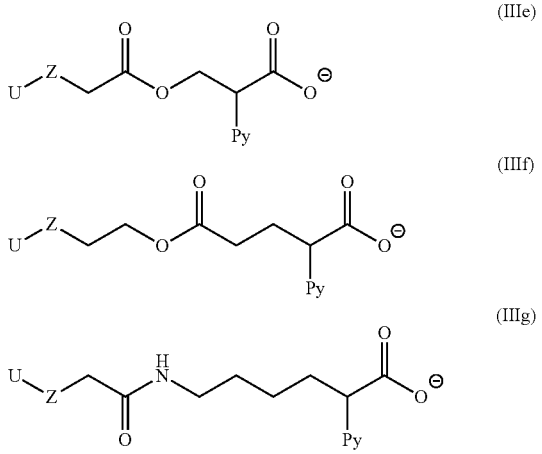

wherein:
R$^1$ at each occurrence is independently selected from H and C$_1$-C$_4$ alkyl;
Z is absent or is a heteroatom;
U is the UV absorbing moiety; and
Py is the ethylenically unsaturated polymerisable moiety.

As shown above in formulae (IIIa), (IIIb), (IIIc), (IIId), (IIIe), (IIIf) and (IIIg), Z may be absent or it may be a heteroatom. The type of Z group may be selected to suit a particular attachment strategy for linking the linker (L) with the UV absorbing moiety (U).

In some embodiments of formulae (IIIa), (IIIb), (IIIc), (IIId), (IIIe), (IIIf) and (IIIg), Z is absent. In such embodiments, the UV absorbing moiety (U) is directly linked to the carbon atom beta to the oxygen atom of the ester in formulae (IIIa) to (IIIg).

In some embodiments of formulae (IIIa), (IIIb), (IIIc), (IIId), (IIIe), (IIIf) and (IIIg), Z is present and is a heteroatom selected from the group consisting of O, N, S and P. In one embodiment, Z is oxygen (O).

In each of formulae (IIIa), (IIIb), (IIIc), (IIId), (IIIe), (IIIf) and (IIIg), the groups R$^1$, Z, U and Py are independently selected at each occurrence.

In some embodiments, in formulae (IIId) the group R$^1$ at each occurrence is independently selected from H and C$_1$-C$_4$ alkyl. Examples of C$_1$-C$_4$ alkyl are methyl, ethyl, n-propyl, i-propyl, n-butyl, i-butyl and t-butyl. A preferred C$_1$-C$_4$ alkyl is methyl.

In one set of embodiments, the polymerisable UV absorber may preferably comprise an anionic linker of formula (IIIa), (IIIb) or (IIIc).

In one set of embodiments, the ocular lens of the invention comprises a hydrogel having a polymer component comprising polymerised residues of a polymerisable UV absorber of formula (I) in which L is a hydrophilic non-polyalkylene glycol linker comprising a saccharide moiety.

When the hydrophilic non-polyalkylene glycol linker (L) comprises a saccharide moiety, such moieties may be in linear (acyclic) or cyclic form. The saccharide moiety may also be a monosaccharide or a polysaccharide, such as a disaccharide.

In one form, the hydrophilic non-polyalkylene glycol linker comprises a cyclic saccharide moiety, such as a furanose, pyranose or amino sugar moiety. A skilled person would appreciate that furanose, pyranose and amino sugar moieties have a 5-membered or 6-membered ring structure. In a specific embodiment, the hydrophilic non-polyalkylene glycol linker may comprise a glucopyranose, galactopyranose, mannopyranose or glucosamine moiety.

In some embodiments the polymer component of the hydrogel may comprise polymerised residues of a polymerisable UV absorber comprising a hydrophilic non-polyalkylene glycol linker having a moiety of formula (X):

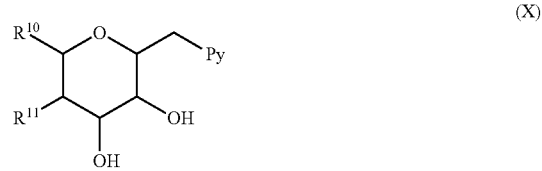

wherein:
Py is the ethylenically unsaturated polymerisable moiety; and
R$^{10}$ and R$^{11}$ are selected from OH and a group of formula (XI), with the proviso that one of R$^{10}$ and R$^{11}$ is the group of formula (XI):

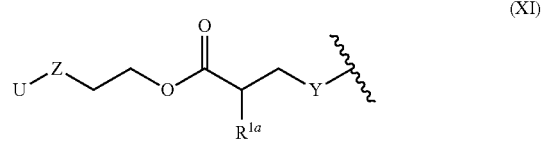

wherein in (XI):
∼∼∼ represents the point of attachment to the 6-membered ring;
Y is a heteroatom;
R$^{1a}$ is selected from H and C$_1$-C$_4$ alkyl;

Z is absent or is a heteroatom (preferably O);
U is the UV absorbing moiety.

In one embodiment of a moiety of formula (X), $R^{10}$ is OH and $R^{11}$ is the group (XI).

In another embodiment of a moiety of formula (X), $R^{10}$ is the group (XI) and $R^{11}$ is OH.

In the group of formula (XI), Y may be a heteroatom. In one preference, Y is selected from O, S and $NR^{1a}$, where $R^{1a}$ is selected from H and $C_1$-$C_4$ alkyl.

Examples of $C_1$-$C_4$ alkyl that may be selected for groups described herein are methyl, ethyl, n-propyl, i-propyl, n-butyl, i-butyl and t-butyl.

For formulae (X) and (XI), the groups Z, U and Py are as defined herein.

In some particular embodiments, the polymer component of the hydrogel may comprise polymerised residues of a polymerisable UV absorber comprising a hydrophilic non-polyalkylene glycol linker having a structure of formula (Xa) or (Xb):

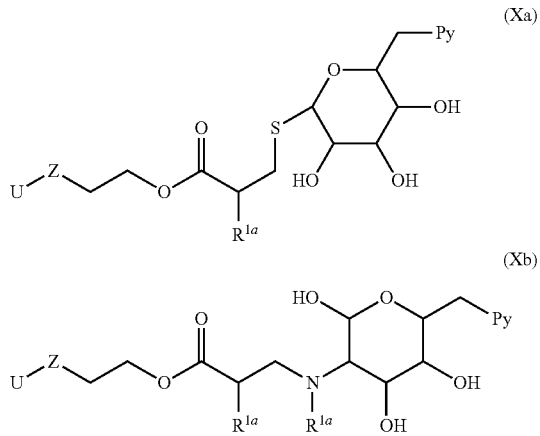

wherein in formula (Xa) and (Xb):
$R^{1a}$ at each occurrence is independently selected from H and $C_1$-$C_4$ alkyl;
Z is absent or is a heteroatom (preferably O);
U is the UV absorbing moiety; and
Py is the ethylenically unsaturated polymerisable moiety.

As shown formulae (X), (Xa) and (Xb), Z may be absent or it may be a heteroatom. The type of Z group may be selected to suit a particular attachment strategy for linking the linker (L) with the UV absorbing moiety (U).

In some embodiments of a linker of formulae (X), (Xa) and (Xb), Z is absent. In such embodiments, the UV absorbing moiety (U) is directly linked to the carbon atom beta to the oxygen atom of the ester in formulae (Xa) and (Xb).

In some embodiments of a linker of formulae (X), (Xa) and (Xb), Z is present and is a heteroatom selected from the group consisting of O, N, S and P. In one embodiment, Z is oxygen (O).

In some embodiments of a linker of formulae (X), (Xa) and (Xb), $R^{1a}$ can be $C_1$-$C_4$ alkyl. Exemplary $C_1$-$C_4$ alkyl may be selected from methyl, ethyl, n-propyl, i-propyl, n-butyl, i-butyl and t-butyl. A preferred $C_1$-$C_4$ alkyl is methyl. Where there is more than one Ria each $R^{1a}$ group can be independently selected at each occurrence.

The polymerisable UV absorber of formula (I) also comprises a UV absorbing moiety (U). The UV absorbing moiety is capable of absorbing radiation in the UV range to impart UV absorbing capabilities to the ocular lens of the invention. Typically, UV radiation exists in wavelengths of from 10-400 nm.

In order for the ocular lens of the invention to have effective UV blocking performance, it can be useful for the UV absorbing moiety to be selected from those capable of absorbing radiation in the UV-A and/or UV-B range. A skilled person would understand that radiation in the UV-B range has a wavelength in the range of from about 280-315 nm, while radiation in the UV-A range has a wavelength in the range of from about 315-380 nm.

In some embodiments, the UV absorbing moiety may belong to a class selected from the group consisting of benzotriazole, benzophenone, triazine, avobenzone, benzylidene, avobenzene, salicylate, anthraniliate, chloroaniline, cyanodiphenyl, benzimidazole, oxanilide, phenyl benzothiazole, and benzothiazole.

In particular embodiments, the UV absorbing moiety (U) belongs to a class selected from benzotriazole and benzophenone. In such embodiments the UV absorbing moiety (U) may thus be a benzotriazole or benzophenone moiety. A preferred benzotriazole moiety may be hydroxyphenyl benzotriazole moiety.

In some embodiments the polymerisable UV absorber may comprise a UV absorbing moiety having a structure of formula (IV):

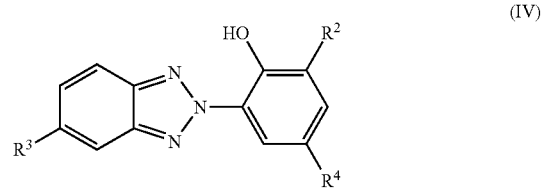

wherein
$R^2$ is selected from H and $C_1$-$C_5$ alkyl;
$R^3$ or $R^4$ represent an attachment point to the linker (L), and wherein:
if $R^3$ is the attachment point to the linker (L), then $R^4$ is selected from H, alkyl and alkoxy; and
if $R^4$ is the attachment point to the linker (L), then $R^3$ is selected from H, halo (preferably chloro) and $CF_3$.

A UV absorbing moiety of formula (IV) may be considered to be a hydroxyphenyl benzotriazole moiety.

It will be appreciated the hydrophilic non-polyalkylene glycol linker can be linked to the UV absorbing moiety of formula (IV) via attachment at either the benzothiazole or hydroxyphenyl rings of the moiety.

In one set of embodiments, the linker (L) is linked to the UV absorbing moiety of formula (IV) via attachment at the benzothiazole ring. In such embodiments, $R^3$ is linked to the linker (L). In such embodiments, $R^4$ can be selected from the group consisting of H, alkyl and alkoxy.

The hydrophilic non-polyalkylene glycol linker (L) linked to the UV absorbing moiety of formula (IV) may be selected from any one of the linkers described herein. For example, the linker may be selected from those of formula (IIIa), (IIIb), (IIIc), (IIId), (IIIe), (IIIf), (IIIg), (Xa) and (Xb), as described herein.

In one embodiment, the ocular lens may comprise a hydrogel having a polymer component comprising polymerised residues of a polymerisable UV absorber of formula (IVa):

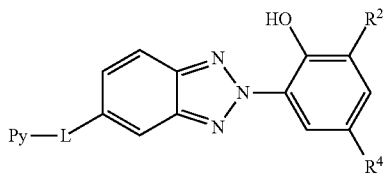

(IVa)

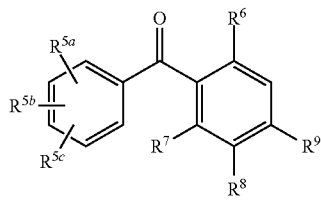

(V)

wherein
- $R^2$ is selected from H and $C_1$-$C_5$ alkyl;
- $R^4$ is selected from H, alkyl and alkoxy;
- L is a hydrophilic non-polyalkylene glycol linker comprising an anionic, a zwitterionic or a saccharide moiety; and
- Py is an ethylenically unsaturated polymerisable moiety.

In one form of formula (IV) or (IVa), $R^4$ may be $C_1$-$C_4$ alkyl, such as methyl, ethyl, n-propyl, i-propyl, n-butyl, i-butyl, t-butyl, and allyl.

In one form of formula (IV) or (IVa), $R^4$ may be $C_1$-$C_4$ alkoxy, such as methoxy, ethoxy, n-propoxy, i-propoxy, n-butoxy, i-butoxy and t-butoxy.

In another set of embodiments, the linker (L) is linked to the UV absorbing moiety of formula (IV) via attachment at the hydroxyphenyl ring. In such embodiments, $R^4$ is linked to the linker (L). In such embodiments, $R^3$ can be selected from the group consisting of H, halo (e.g. bromo, chloro, fluoro, iodo), and $CF_3$.

In another embodiment the ocular lens may comprise a hydrogel having a polymer component comprising polymerised residues of a polymerisable UV absorber of formula (IVb):

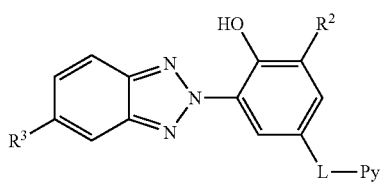

(IVb)

wherein
- $R^2$ is selected from H and $C_1$-$C_5$ alkyl;
- $R^3$ is selected from H, halo, $CF_3$;
- L is a hydrophilic non-polyalkylene glycol linker comprising an anionic, a zwitterionic or a saccharide moiety; and
- Py is an ethylenically unsaturated polymerisable moiety.

In one form of formula (IVb), $R^2$ may be $C_1$-$C_4$ alkyl, such as methyl, ethyl, n-propyl, i-propyl, n-butyl, i-butyl, t-butyl, and allyl.

In the UV absorbers of formulae (IVa) or (IVb), the linker (L) may be selected from those of formula (IIIa), (IIIb), (IIIc), (IIId), (IIIe), (IIIf), (IIIg), (Xa) and (Xb), as described herein. In one preference, the group Z in such linkers is an oxygen heteroatom (O). The UV absorbing moiety of formulae (IVa) or (IVb) and the linker (L) may thus be linked to one another via the O heteroatom.

In some other embodiments the polymerisable UV absorber may comprise a UV absorbing moiety having a structure of formula (V):

wherein
- $R^{5a}$, $R^{5b}$ and $R^{5c}$ are each independently selected from H, halo (e.g. bromo, chloro, fluoro or iodo), hydroxyl, carboxylate, sulfonate, $C_1$-$C_6$ alkyl, $C_1$-$C_6$ alkoxy, $C_6$-$C_{10}$ aryl, and substituted aryl groups;
- $R^6$ and $R^7$ are each independently selected from H and OH with the proviso that $R^6$ and $R^7$ are not identical;
- $R^8$ is selected from H and sulfonate; and
- $R^9$ is the attachment point to the linker (L).

A UV absorbing moiety of formula (V) may be considered to be a benzophenone moiety.

As shown in formula (V), the hydrophilic non-polyalkylene glycol linker (L) can be linked to the UV absorbing moiety via attachment at $R^9$.

In a particular embodiment, the ocular lens may comprise a hydrogel having a polymer component comprising polymerised residues of a polymerisable UV absorber of formula (Va):

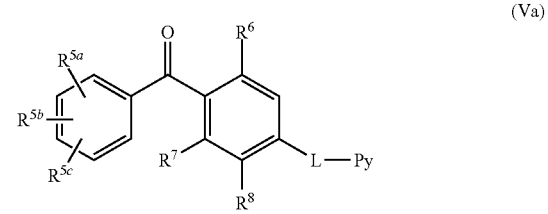

(Va)

wherein
- $R^{5a}$, $R^{5b}$ and $R^{5c}$ are each independently selected from H, halo (e.g. bromo, chloro, fluoro or iodo), hydroxyl, carboxylate, sulfonate, $C_1$-$C_6$ alkyl, $C_1$-$C_6$ alkoxy, $C_6$-$C_{10}$ aryl, and substituted aryl groups;
- $R^6$ and $R^7$ are each independently selected from H and OH with the proviso that $R^6$ and $R^7$ are not identical;
- $R^8$ is selected from H and sulfonate;
- L is a hydrophilic non-polyalkylene glycol linker comprising an anionic, a zwitterionic or a saccharide moiety; and
- Py is an ethylenically unsaturated polymerisable moiety.

In some embodiments of a UV absorber of formula (Va), the linker (L) may be selected from those of formula (IIIa), (IIIb), (IIIc), (IIId), (IIIe), (IIIf), (IIIg), (Xa) and (Xb), as described herein, wherein the group Z in the linker is an oxygen heteroatom (O). The linker (L) and UV absorbing moiety are therefore linked to one another via the O heteroatom.

In addition to the hydrophilic non-polyalkylene glycol linker (L) and the UV absorbing moiety (U) the polymerisable UV absorber of formula (I) also comprises an ethylenically unsaturated polymerisable moiety (Py), which would generally be a terminal moiety. The ethylenically unsaturated polymerisable moiety enables the polymerisable UV absorber to covalently react with other monomers under suitable polymerisation conditions to facilitate formation of a polymer. An exemplary polymerisation condition is free radical polymerisation.

The ethylenically unsaturated polymerisable moiety may be selected from any moiety suitable to undergo reaction via free radical polymerisation.

In one set of embodiments, the ethylenically unsaturated polymerisable moiety (Py) in the polymerisable UV absorber of formula (I) may be selected from the group consisting of allyl, vinyl, acryloyl, methacryloyl, and styrenyl.

Polymerisable acryloyl moieties described herein may be acrylate or acrylamido moieties. Similarly, polymerisable methacryloyl moieties described herein may be methacrylate or methacrylamido moieties.

Some particular examples of polymerisable UV absorbers of formula (I) useful for preparing the ocular lenses described herein are shown in Scheme 1.

Scheme 1. Examples of polymerisable UV absorbers of formula (I)

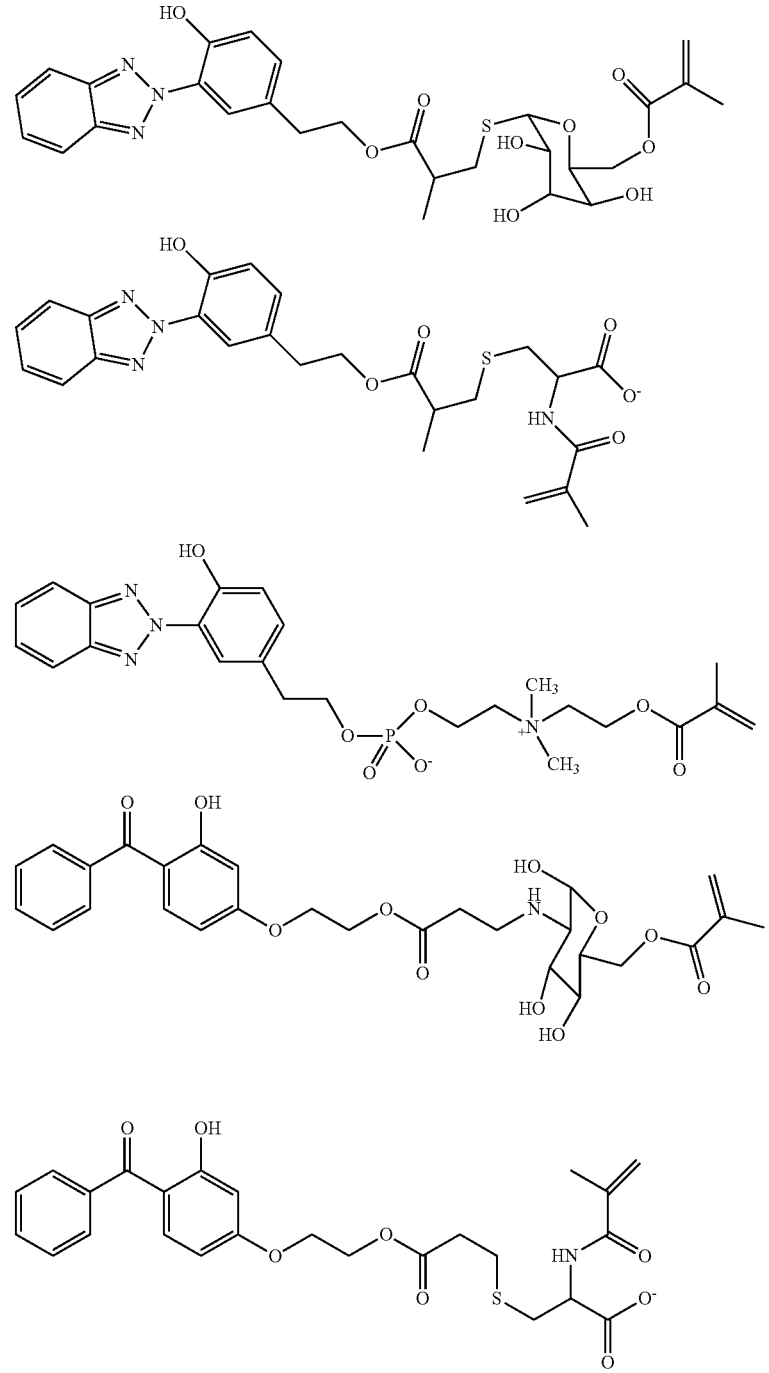

-continued

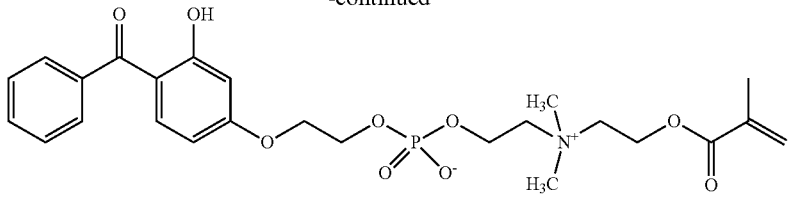

An ocular lens of the invention may comprise a hydrogel having a polymer component comprising polymerised residues derived from two or more polymerisable UV absorbers. In such embodiments, the hydrogel polymer may comprise polymerised residues derived from at least one polymerisable UV absorber of formula (I) and at least one other polymerisable UV absorber, which are present in the hydrogel in combination.

The at least one other polymerisable UV absorber may be another polymerisable UV absorber of formula (I) having a different chemical structure, such as a different UV absorbing moiety and/or a different non-polyalkylene glycol linker.

Alternatively, the at least one other polymerisable UV absorber may be a conventional, known or commercially available polymerisable UV absorber, which is used in combination with the polymerisable UV absorber of formula (I).

Thus in some embodiments of an ocular lens according to the invention, the hydrogel polymer comprises polymerised residues derived from at least two different polymerisable UV absorbers, wherein at least one of the polymerisable UV absorbers is a polymerisable UV absorber of formula (I).

In some embodiments, an ocular lens of the invention may comprise a hydrogel having a polymer component comprising polymerised residues derived from at least two different polymerisable UV absorbers of formula (I). For example, the polymer component of the hydrogel may comprise polymerised residues of a first polymerisable UV absorber having a benzotriazole UV absorbing moiety and a second polymerisable UV absorber having a benzophenone UV absorbing moiety. The incorporation of two or more different UV absorbers in the hydrogel polymer may be advantageous to enable the UV absorbing capability of the ocular lens to be adjusted and optimised, particularly for the UV-A and UV-B range.

In some embodiments, an ocular lens of the invention may comprise a hydrogel having a polymer component comprising polymerised residues derived from at least one polymerisable UV absorbers of formula (I) and at least one other polymerisable UV absorber that is not of formula (I). In such embodiments, the at least one other polymerisable UV absorber may be a known, commercially available UV absorber. Examples of commercially available polymerisable UV absorbers that may be used in combination with the UV absorbers of formula (I) to form hydrogel polymers for the UV absorbing ocular lenses are 2-[3-(2H-benzotriazol-2-yl)-4-hydroxyphenyl]ethyl methacrylate (HB7) (CAS: 96478-09-0) and 2-(4-benzoyl-3-hydroxyphenoxy)ethyl acrylate (BP15) (CAS: 16432-81-8).

The hydrogel polymer for the ocular lens of the invention may comprise an effective amount of a polymerisable UV absorber of formula (I), optionally in combination with at least one other polymerisable UV absorber.

In general, the total amount of polymerisable UV absorber incorporated in the polymer component of the hydrogel is sufficient to enable the ocular lens of the invention to achieve an effective level of UV blocking performance. In some embodiments, an effective level of UV blocking means that the ocular lens of the invention at least meets ISO Class II specifications. Thus the ISO Class II standard can represent the minimum level of UV blocking performance for the ocular lens. In some embodiments, the ocular lens can exceed ISO Class II specifications. In some embodiments, the ocular lens of the invention may meet ISO Class I specifications for UV absorbing lenses. It can be desirable for the ocular lens to meet the ISO Class I or Class II specification without an observable yellowish tint being imparted to the lens.

In some embodiments, the ocular lens of the invention has an average UV transmittance of less than 10 percent in the UV-A range and an average UV transmittance of less than 1.0 percent in the UV-B range.

The total amount of polymerisable UV absorber used may depend on the polymer base, thickness of the ocular lens, water and solids content, and desired level of UV absorption.

Useful amounts of polymerisable UV absorber for incorporation in an ocular lens can be selected to confer a desirable level of UV blocking performance. For contact lenses and intraocular lenses made primarily from acrylate and methacrylate-based hydrogel polymers, the hydrogel can comprise from about 0.01 to 25 wt %, preferably from about 0.1 to 10 wt %, of polymerised residues derived from one or more polymerisable UV absorbers in some embodiments.

In one embodiment, the polymerisable UV absorber of formula (I) is used on its own to confer UV absorbing properties to the ocular lens. In such embodiments, the hydrogel polymer comprises from about 0.01 to 25 wt %, preferably from about 0.1 to 10 wt %, of polymerised residues derived from a polymerisable UV absorber of formula (I), based on the total weight of monomeric units in the hydrogel polymer.

In other embodiments, a combination of two or more different polymerisable UV absorbers may be used to confer UV absorbing properties to the ocular lens. When two or more different polymerisable UV absorbers are incorporated in the hydrogel polymer, the total amount of polymerised residues derived from the UV absorbers may be in the range of from about 0.01 to 25 wt %, preferably in the range of from about 0.1 to 10 wt %, based on the total weight of monomeric components in the polymer. As described herein, it is a requirement of the invention that at least one of the polymerisable UV absorbers in the combination is of formula (I), such that at least a portion of the polymerised residues in the hydrogel polymer is derived from a UV absorber of formula (I).

In one form, the hydrogel of the ocular lens of the inventions comprises from about 0.0006 to 0.0042 millimoles of one or more polymerisable UV absorber.

When a combination of two or more different polymerisable UV absorbers are incorporated in the hydrogel polymer, the relative amount of polymerisable UV absorber of formula (I) in the combination may be adjusted within a desired concentration range, allowing different UV absorbers to be present in the hydrogel polymer in different ratios.

In another aspect, the present invention also provides a polymerisable UV absorber of formula (I):

U-L-Py  (I)

wherein:
U is a UV absorbing moiety;
L is a hydrophilic non-polyalkylene glycol linker comprising an anionic, a zwitterionic or a saccharide moiety; and
Py is an ethylenically unsaturated polymerisable moiety.

For the polymerisable UV absorber of formula (I), U, L and Py are described herein.

Polymerisable UV absorbers of formula (I) may be prepared using chemical synthetic protocols and techniques known in the art.

It is an advantage that the polymerisable UV absorber of formula (I) is hydrophilic and compatible with other monomers suitable for forming hydrogel polymers. Accordingly, the polymerisable UV absorber of formula (I) can be mixed with those other monomers, thereby allowing a substantially homogeneous monomer composition to be formed. For instance, polymerisable UV absorbers of formula (I) have been found to be soluble in other hydrogel-forming monomers. A homogenous monomer composition may have no evident precipitation or phase separation of the monomer components. The hydrophilicity of the polymerisable UV absorber of formula (I) can help to ensure that a sufficient quantity of the UV absorber can be incorporated in the hydrogel polymer in amounts sufficient to confer a desired level of UV blocking performance while not giving rise to unacceptable changes in the physical and/or chemical properties of the hydrogel polymer. This can help to ensure that the stability, comfort, appearance and/or optical transparency of the ocular lens meet acceptable consumer or industry requirements.

In the ocular lens of the invention, the polymerisable UV absorber is covalently incorporated in the polymeric component of the hydrogel used to form the ocular lens. This prevents the UV absorber from leaching out of the lens material, which may otherwise present both toxicological issues and lead to the loss of UV blocking capability. Such stability is important for ocular lenses, especially for implantable ocular lenses such as intraocular lenses (IOLs).

To form the hydrogel polymer, the polymerisable UV absorber of formula (I) is generally polymerised with one or more co-monomers. The co-monomers are typically ethylenically unsaturated monomers comprising at least one ethylenically unsaturated group.

In some embodiments, a mixture of two or more co-monomers is polymerised with the polymerisable UV absorber of formula (I). For example, the UV absorber may be polymerised with a mono-ethylenically unsaturated monomer and a crosslinking agent.

In another aspect, the present invention provides a hydrogel polymer comprising polymerised residues derived from (i) at least one ethylenically unsaturated monomer, and (ii) a polymerisable UV absorber of formula (I):

U-L-Py  (I)

wherein:
U is a UV absorbing moiety;
L is a hydrophilic non-polyalkylene glycol linker comprising an anionic, a zwitterionic or a saccharide moiety; and
Py is an ethylenically unsaturated polymerisable moiety.

For the polymerisable UV absorber of formula (I), U, L and Py are described herein.

Ethylenically unsaturated monomers for reaction with the polymerisable UV absorber of formula (I) are preferably selected from conventional monomers suitable for forming hydrogel materials for an ocular lens. Such monomers may and generally will comprise a single ethylenically unsaturated moiety and be mono-functional.

In some embodiments, the polymerisable UV absorber of formula (I) and the at least one ethylenically unsaturated monomer is also be polymerised with an ethylenically unsaturated crosslinking agent as a further co-monomer. Conventional crosslinking agents suitable for forming hydrogel materials for ocular lenses can be used.

Crosslinking agents described herein will generally comprise at least two terminal ethylenically unsaturated moieties that will react to facilitate formation of the network polymer component of the hydrogel polymer. In some embodiments, suitable crosslinking agents may comprise at least three ethylenically unsaturated moieties, which are terminal moieties. Crosslinking agents may be considered to be multi-functional. Accordingly, the hydrogel polymer may comprise polymerised residues derived from an ethylenically unsaturated crosslinking agent.

Types of ethylenically unsaturated monomers and crosslinking agent to be copolymerised with the UV absorber of formula (I) and their respective quantities may be selected on the basis of the type of ocular lens to be manufactured.

In some embodiments, hydrogels suitable for an ocular lens of the invention can comprise from about 40 to 80% (w/w) of polymer. That is, the polymer (solids) component can form from about 40 to 80% by weight of the hydrogel. The remainder of the hydrogel will typically be formed of a liquid component (e.g. water) that hydrates the polymer component of the hydrogel. For example, a HEMA hydrogel may comprise about 42 wt % solids component, with the remainder being a liquid component such as water. Additionally, a silicone hydrogel may comprise from 60-80 wt % solids component, with the remainder being a liquid component such as water.

The hydrogel polymer component per se will generally comprise polymerised residues derived from at least one polymerisable UV absorber of formula (I), which are present in the hydrogel polymer together with polymerised residues derived from one or more co-monomers. In some embodiments, the hydrogel polymer (solids) component may comprise from about 20 to 90 wt % of polymerised residues derived from one or more co-monomers, based on the total weight of monomeric units in the polymer.

Co-monomers polymerised with the UV absorber of formula (I) would include ethylenically unsaturated co-monomers as well as crosslinking agent.

The hydrogel polymer component may comprise from about 20 wt % to about 90 wt % of polymerised residues derived from one or more ethylenically unsaturated co-monomers and crosslinking agent, based on the total weight of monomeric units in the polymer. In one embodiment, the hydrogel polymer comprises from about 40 wt % to about 80 wt % of polymerised residues derived from one or more ethylenically unsaturated co-monomers and crosslinking agent, based on the total weight of monomeric units in the polymer.

Polymerised residues derived from the polymerisable UV absorber of formula (I) may form from about 0.01 to 25 wt %, preferably from 0.1 to 10 wt %, of the hydrogel polymer, based on the total amount of monomeric units in the hydrogel polymer.

The polymerisable UV absorber of formula (I) and co-monomers can covalently react under suitable polymerisation conditions to become polymerised residues in the resultant hydrogel polymer. A skilled person would be able to select polymerisation techniques and conditions suitable for forming a hydrogel polymer useful for an ocular lens. An example of a process for forming the hydrogel polymer is described below.

Numerous ethylenically unsaturated monomers can be polymerised with the UV absorber of formula (I) to form the hydrogel polymer. In some embodiments, it is preferred that the UV absorber of formula (I) is polymerised with a hydrophilic ethylenically unsaturated co-monomer.

In one form, the UV absorber of formula (I) can be polymerised with an ethylenically unsaturated monomer selected from the group consisting of acryloyl monomers, methacryloyl monomers, vinylic monomers, silicone-containing monomers, and combinations thereof.

The hydrogel polymer formed by polymerising the UV absorber of formula (I) and at least one ethylenically unsaturated co-monomer may be considered to be an acrylic or silicone hydrogel polymer, depending on the nature of the monomers used to prepare the polymer.

Representative ethylenically unsaturated monomers that may be copolymerised with the polymerisable UV absorber of formula (I) to produce a hydrogel polymer for a UV absorbing ocular lens include, without limitation:
(a) acryloyl and methacryloyl monomers such as acrylic acid, methacrylic acid, acrylamide and methacrylamide, as well as ester and amide derivatives thereof;
(b) silicone substituted acrylic or methacrylic esters;
(c) fluorinated acrylic or methacrylic esters; and
(d) vinyl or vinylidene compounds such as vinyl pyrrolidones, vinyl silanes, vinyl sulfones, vinyl alcohols or esters, and the like.

Specific examples of hydrogel-forming ethylenically unsaturated monomers include acrylic acid, methacrylic acid, hydroxyalkyl (meth)acrylates (such as 2-hydroxyethyl acrylate and 2-hydroxyethyl methacrylate), N-vinyl pyrrolidone, alkyl (meth)acrylates (such as methyl acrylate, methyl methacrylate, tridecylmethacrylate, tert-butyl methacrylate and cyclohexyl methacrylate), aryl (meth)acrylates (such as benzyl methacrylate), aminoalkyl (meth)acrylate (such as 2-(dimethylamino)ethyl acrylate, methacrylamide propyl trimethyl ammonium chloride and 2-(dimethylamino)ethyl methacrylate), (meth)acrylamides (such as N, N-dimethyl-acrylamide), methacryloxyethyl succinic acid, 2-methacryloyloxyethylhexahydrophtalic acid, methacryloyloxymethyl phosphate,) silicone (meth)acrylates (such as tris(trimethylsiloxy)silylpropyl methacrylate) and 3-(3-methacryloxy-2-hydroxypropoxy)propyl bis(trimethylsiloxyl)methyl silane, glyceryl (meth)acrylate, fluorine-atom containing (meth)acrylates (such as trifluroethyl(meth)acrylate)), vinyl-containing monomers (such as vinyl acetate, vinyl butyrate, N-vinylpyrrolidone (NVP), N-vinyl-N-methylacetamide, N-vinyl-N-ethylacetamide, N-vinyl-N-ethylformamide and N-vinylformamide), or a combination of such monomers. Other hydrogel-forming monomers may be used.

In some embodiments, the hydrogel polymer comprises polymerised residues derived from an ethylenically unsaturated monomer selected from the group consisting of acrylic acid, methacrylic acid, 2-hydroxyethyl acrylate, 2-hydroxyethyl methacrylate, dimethylaminoethyl methacrylate, methacrylamide propyl trimethyl ammonium chloride, methacryloxyethyl succinic acid, methacryloyloxymethyl phosphate, N, N-dimethylacrylamide, tris(trimethylsiloxy) silylpropyl methacrylate, and combinations thereof.

A number of crosslinking agents may be used for formation of the hydrogel polymer. Suitable crosslinking agents may include, for example: acrylate and methacrylate-based cross-linking agents such as ethyleneglycol diacrylate, diethyleneglycol diacrylate, triethyleneglycol diacrylate, propyleneglycol diacrylate, dipropyleneglycol diacrylate, trimethylolpropane triacrylate, pentaerythritol triacrylate, pentaerythritol tetraacrylate, dipentaerythritol hexaacrylate, bis(acryloxy)alkylpoly(dimethyl siloxane), ethyleneglycol dimethacrylate, diethyleneglycol dimethacrylate, triethyleneglycol dimethacrylate, propyleneglycol dimethacrylate, dipropyleneglycol dimethacrylate, trimethylolpropane trimethacrylate, pentaerythritol trimethacrylate, pentaerythritol tetramethacrylate, dipentaerythritol hexamethacrylate, and bismethacryloxyalkylpoly(dimethyl siloxane); and vinyl-based cross-linking agents such as allyl methacrylate, diallyl maleate, diallyl fumarate, diallyl succinate, diallyl phthalate, triallyl cyanurate, triallyl isocyanurate, diethylene glycol bis(allyl carbonate), triallyl phosphate, triallyl trimellitate, diallyl ether, N—N-diallylmelamine and divinyl benzene. Other crosslinking agents may be used. A combination of two or more crosslinking agents may also be used.

The crosslinking component may form at least 0.1% by weight of the hydrogel polymer and, depending on the identity and concentration of the remaining components and desired physical properties, can range up to about 20% by weight. In some embodiments, the hydrogel polymer comprises from about 0.1 to about 10 wt %, or from about 0.2 to about 5 wt % of polymerised residues derived from a crosslinking agent.

In one embodiment, a monomer mixture for forming a hydrogel suitable for an ocular lens of the invention comprises:
(a) from about 0.1 to about 10 wt % of a polymerisable UV absorber of formula (I);
(b) from about 10 to about 99.99 wt % of at least one ethylenically unsaturated monomer; and
(c) from about 0.2 to about 5 wt % of a crosslinking agent.

In a particular embodiment, the ocular lens comprises an acrylic hydrogel formed from a monomer mixture comprising a polymerisable UV absorber of formula (I) and one or more acryloyl and/or methacryloyl monomers.

One exemplary monomer mixture for forming a hydrogel may comprise:
(a) from about 2 to 6 wt % of a polymerisable UV absorber of formula (I);
(b) from about 90 to about 98 wt % of 2-hydroxyethyl methacrylate;
(c) from about 2 to 5 wt % of methacrylic acid; and
(d) from about 0.2 to about 1 wt % of trimethyloylpropane trimethacrylate.

Initiation of the polymerisation between the polymerisable UV absorber of formula (I) and desired co-monomers can be achieved using a suitable initiator. The initiator may be a thermal or photo-initiator. A preferred thermal initiator is an azo type or organic peroxide type initiator, which is capable of initiating the polymerisation reaction at a relatively low temperature, such as in the range of from about 30 to 90° C. An exemplary initiator is azoisobisbutyronitrile (AIBN), although other initiators can be used. Initiators are typically present in conventional amounts, which may be an amount of about 1% (w/w) or less. The total amount of initiator is customarily not included when determining the amounts of other ingredients.

Polymerisation may take place by any of the methods well known within the ocular device industry, e.g., by heat or UV light. Polymerisation may be conducted at a temperature in the range of from about 25° to 140° C., more preferably 30° to 100° C., for 5 minutes to 96 hours, more preferably from about 1 to 24 hours. In addition, known moulding or casting techniques suitable for forming ocular lenses can be used. The exact manner used for polymerisation and lens shaping is a matter of choice and is not critical to this invention.

A skilled person would understand that hydrogels are generally formed by mixing a desired quantity of one or more hydrogel-forming monomers together and polymerising the monomers in the mixture. The monomers may be mixed together in neat form, or they may be dissolved or dispersed in a solvent to form a solution. A suitable solvent may be an organic solvent such as ethanol, or an aqueous solvent such as water. Organic solvents used in the preparation of the hydrogels can be removed in a subsequent washing step after the hydrogel polymer is formed.

Known methods may be employed to prepare the hydrogel and the ocular lens of the invention. For example, the polymerisable UV absorber of formula (I) and other hydrogel-forming monomers can be mixed with a selected initiator in a suitable solvent. The resultant solution is then introduced into a lens-shaped mould and the mixture of monomers polymerised in the mould. Polymerisation then takes place at a temperature in a range of from about 400 to 100° C., for a time period of from about 2 to 6 hours. The formed polymer is then removed from the mould and hydrated in an aqueous liquid to form the hydrogel in the desired shape of an ocular lens. The aqueous liquid may be physiologically acceptable liquid. As the mould can be suitably configured to enable the hydrogel to be fabricated in the form of an ocular lens, further post-polymerisation shaping of the hydrogel may not be necessary.

If desired, other additives or components known in the art may be included with the mixture of monomers. Such additives or other components may include for example, diluents, stabilisers, dyes, pigments, antimicrobial compounds, release agents and so forth.

Hydrogels having a polymer component formed with a polymerisable UV absorber of formula (I) can possess hydrophilicity and optical properties suitable for the manufacture of ocular lenses such as contact lenses and intraocular lenses. The properties of the hydrogel can be imparted to the ocular lens fabricated with the hydrogel material. As the hydrogel has UV absorbing capabilities, contact lenses and intraocular lenses formed with the hydrogel are thus also UV absorbing contact lenses or intraocular lenses.

A hydrogel having a polymer component incorporating the polymerisable UV absorber of formula (I), which is suitable for the formation of an UV absorbing ocular lens, is desirably acceptable to the ophthalmic industry. By this is meant that the UV absorber-containing hydrogel can achieve a level of UV blocking performance that meets accepted industry standards, yet the hydrogel also retains a number of desirable properties, which can help to confer suitability to the hydrogel as a material for formation of an ocular lens.

In particular, it has been found that hydrogel properties beneficial for ocular lens applications, such as water content, optical transparency, and colour, are not unacceptably altered as a result of the presence of the UV absorber of formula (I) in the hydrogel polymer. In one set of embodiments, the water content, optical transparency and colour of the UV absorber-containing hydrogel are within an acceptable range of variation, relative to that of a base hydrogel having a polymer component containing no UV absorber.

To determine whether a hydrogel having a polymer component comprising a polymerisable UV absorber of formula (I), and hence a UV absorbing ocular lens of the invention, is likely to be industrially acceptable, it can in some embodiments be convenient to compare the properties of the hydrogel and/or ocular lens fabricated with the hydrogel, with that of a blank sample.

As used herein, the term "blank sample" refers to a sample comprising a hydrogel having a polymer component prepared with identical hydrogel forming monomers as that employed for formation of a test UV-absorber containing hydrogel, however with the exception that it contains no UV absorber. The blank samplample can be considered to be a base hydrogel, since the polymer component has no UV absorber. To be useful as a reference for assessment of a test sample, the blank sample should in general have equivalent dimensions (e.g. area, diameter and/or thickness) to that of the test sample material. In some embodiments, the blank sample may represent a commercially acceptable product having defined product specifications. The blank sample is thus used for comparative purposes when assessing whether a UV absorber-containing hydrogel, or an ocular lens containing the UV absorber-containing hydrogel, is likely to meet desired product specifications and performance criteria.

It has been found that one advantage of a UV absorbing ocular lens of the invention is that it has greater than 75% transparency to visible light (radiation wavelengths of from 400-500 nm) at an average thickness of about 100 µm. In some embodiments, the ocular lens in accordance with the invention has an average visible light transmittance at 400-500 nm of at least 78%, at least 80%, at least 85%, at least 90%, at least 95%, or at least 98%, when measured at an average thickness of about 100 µm. A high visible light transmittance (>75% transmittance) can be an indicator of optical transparency. It is preferred that an ocular lens of the invention does not exhibit an opaque or hazy appearance as this can be detrimental to the performance of the lens.

The visible light transmittance of the ocular lens may be determined by assessing the ocular lens per se, or a hydrogel useful for forming the ocular lens, using UV-visible spectroscopy, and determining the average light transmittance (% T) in the wavelength range of from 400 to 500 nm.

The wavelength range of 400 to 500 nm is selected for assessing visible light transmission as this range can also usefully provide an indicator of the presence of any yellow tint in the hydrogel per se, or an ocular lens comprising the hydrogel. The presence of a yellow tint can be visually confirmed by placing the hydrogel or ocular lens on a white surface, such as white piece of paper. It is desirable that the ocular lens of the invention has no visually discernible yellow tint when the lens is assessed against a white background, as a yellow tint can detract from the appearance of the lens and thus make it less appealing to consumers. Thus it is another advantage that a UV absorbing ocular lens of the invention has no visually observable yellow tint.

It is yet another advantage of a UV absorbing ocular lens of the invention that it displays a level of optical transparency that is acceptable to the ophthalmic industry. Optical transparency can be ascertained by determining the average visible light transmittance at 400 to 500 nm for a hydrogel having a polymer component comprising a selected polymerisable UV absorber (% $T_{sample}$), and comparing the transmittance result for the UV absorber-containing hydrogel sample with the result obtained for a blank sample (% $T_{Blank}$) under the same test conditions.

The difference in % T values (ΔT %) between the blank sample (% $T_{Blank}$) and the UV-absorber containing sample (% $T_{sample}$) is calculated according to the following equation:

$$\Delta T \% = T \%_{Blank} - T \%_{sample}$$

It is desirable that a UV absorbing ocular lens of the invention, or a hydrogel having a polymer component comprising a UV absorber of formula (I) that is suitable for forming the ocular lens, have an optical transparency that is within an acceptable, predetermined range of variation, relative to the blank sample. That is, any change in optical transparency (ΔT %) that may be exhibited by the test sample relative to the blank sample is within defined and acceptable performance limits.

In some embodiments, a UV absorbing ocular lens of the invention, or a hydrogel having a polymer component comprising a UV absorber of formula (I) suitable for forming the ocular lens, has an optical transparency that is at least equivalent to that of a blank sample.

In some embodiments, a UV absorbing ocular lens of the invention, or a hydrogel having a polymer component comprising a UV absorber of formula (I) suitable for forming the ocular lens, may exhibit a reduction (decrease) in optical transparency compared to the blank sample.

Where a UV absorbing ocular lens of the invention, or a hydrogel having a polymer component comprising a UV absorber of formula (I), exhibits a reduction in optical transparency, it is preferred that there is not more than a 20% reduction in optical transparency, relative to the blank. This may be expressed as a requirement whereby the ocular lens or the hydrogel exhibits a change in visible light transmittance (i.e. ΔT %) that is >-20%, relative to a blank sample. A hydrogel sample that has a greater than 20% reduction in optical transparency relative to a blank may indicate a hazy or opaque hydrogel.

An ocular lens of the invention is also hydrophilic due to the hydrogel material and is able to be solvated by water. The hydrophilicity of the ocular lens can be assessed by determining equilibrium water content (EWC), which provides a measure of how readily the lens material can be solvated by water. The EWC can be calculated from a hydrogel sample's wet mass ($M_{wet}$) and dry mass ($M_{dry}$) according to the following equation:

$$EWC = \frac{M_{wet} - M_{dry}}{M_{wet}} \times 100\%$$

In some embodiments, an ocular lens of the invention has a EWC selected from at least about 20%, at least about 25%, at least about 30%, at least about 35%, at least about 40%, at least about 45%, at least about 50%, or at least 55%.

It is yet another advantage of a UV absorbing ocular lens of the invention that it has a level of water content (EWC) that is acceptable to the ophthalmic industry. Ocular lenses of the present invention preferably have a EWC that is not unacceptably altered in comparison to a blank sample. In one preference, ocular lenses of the invention have an EWC that is at least equivalent to, or greater than, the EWC of a blank sample. In some embodiments, the ocular lens of the invention possesses an acceptable EWC that enables it to at least meet established EWC specifications for commercial ocular lenses.

In order to assess whether an ocular lens, or a hydrogel suitable for forming the ocular lens, has a water content (EWC) that is likely to be acceptable, it can be convenient to determine the difference in EWC values between a blank sample ($EWC_{Blank}$) and a test UV absorber-containing hydrogel sample prepared with a selected polymerisable UV-absorber ($EWC_{sample}$). The difference in EWC (ΔWC %) between the blank sample and the test sample can thus be determined according to the following equation:

$$\Delta WC \% = EWC_{Blank} - EWC_{sample}$$

It is desirable that a UV absorbing ocular lens of the invention, or a hydrogel having a polymer component comprising a UV absorber of formula (I) suitable for forming the ocular lens, has an equilibrium water content (EWC) that is within an acceptable, predetermined range of variation, relative to the blank sample. Accordingly, any change in water content (ΔWC %) that may be exhibited by the UV absorber-containing sample relative to the blank sample is within defined and acceptable performance limits.

In some embodiments, a hydrogel having a polymer component comprising a UV absorber of formula (I), or a UV absorbing ocular lens comprising the said hydrogel, may exhibit an increase or a decrease in equilibrium water content, compared to the blank sample.

In one set of embodiments, a UV absorbing ocular lens of the invention, or a hydrogel having a polymer component comprising a UV absorber of formula (I) suitable for forming the ocular lens, exhibits an increase or a decrease in equilibrium water content of not more than 10%, or not more than 5%, relative to that of the blank sample. This may be expressed as a requirement that the change in water content (ΔWC %) between the ocular lens of the invention and the blank sample be within ±10%, or +5%, relative to the blank sample.

It has advantageously been found that a hydrophilic polymerisable UV absorber having a non-polyalkylene glycol linker can allow hydrogel polymers having a higher concentration of UV absorbing moieties to be formed, while not producing a detrimental effect on the EWC of the hydrogel.

Ocular lenses of the invention may be contact lenses. Contact lenses are hydrophilic lenses, and can be soft lenses or hard (i.e. rigid-gas-permeable (RGP)) lenses depending on the monomer or combination thereof with which the polymerisable UV absorber described herein is copolymerised.

Contact lenses can include those for correcting defective visual acuity and so-called "bandage lenses" used to treat eye disorders, as well as cosmetic lenses used for purposes such as changing apparent eye colour.

Ocular lenses of the invention may be intraocular lenses (IOLs). IOLs are implantable lenses and can be of any design capable of being rolled or folded into a small cross section that can fit through a relatively smaller incision. For example, the IOLs can be of what is known as a one piece or multipiece design, and comprise optic and haptic components. The optic is that portion which serves as the lens. The haptics are attached to the optic and hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material.

UV absorbing ocular lenses of the invention, including UV absorbing contact lenses and intraocular lenses, may have one or more advantages. These include:

- high UV absorption in the UV-A and/or UV-B range of wavelengths that provide for effective UV blocking performance meeting at least ISO Class II standards;
- water content that is not unacceptably reduced, or is higher than that observed for a blank hydrogel-based ocular lens that does not contain a UV absorber, thereby allowing the ocular lens of the invention to meet industrially acceptable EWC product specifications;
- high optical transparency (>75% visible light transmission in the range of from 400-500 nm);
- visible light transmittance that is not unacceptably reduced in comparison to a blank hydrogel-based ocular lens that does not contain a UV absorber, thereby allowing the ocular lens of the invention to meet industrially acceptable optical transparency product specifications;
- no visible yellow tint;
- usefulness as soft lenses.

The above advantages can help to ensure that an ocular lens of the invention, which is formed with a hydrogel having a polymer component comprising a UV absorber of formula (I), can at least meet a number of commercially important and industrially acceptable performance criteria for UV absorbing lenses.

In some embodiments, the ocular lens of the invention may possess not only the required UV absorbing ability, but also a water content and a level of optical transparency that is within an acceptable and predetermined range relative to a blank sample, as well as no visually discernible yellow appearance.

The invention will now be described with reference to the following examples. However, it is to be understood that the examples are provided by way of illustration of the invention and that they are in no way limiting to the scope of the invention.

EXAMPLES

Chemicals and Materials:

2-Hydroxyethyl methacrylate (HEMA), methacrylic acid (MAA), trimethylolpropane trimethyacrylate (TMPTMA), azoisobutyronitrile (AIBN), 2-[3-(2H-benzotriazol-2-yl)-4-hydroxyphenyl]ethyl methacrylate (HB-7), 2-(4-benzoyl-3-hydroxyphenoxy)ethyl acrylate (BP15), 1-thio-β-D-glucose sodium salt, dimethylphenyl phosphine, methacrylic anhydride, pyridine, dimethyl sulfoxide, L-cysteine, N,N-dimethylformamide (DMF), N-hydroxysuccinimidyl methacrylate, triethylamine (TEA), 2-bromo acetyl chloride, triethylamine (TEA), dichloromethane (DCM), 2-(dimethylamino)ethyl methacrylate (DMAEMA), acetonitrile, sodium hydroxide (NaOH), hydrochloric acid (HCl), magnesium sulfate (MgSO$_4$), 2-chloro-2-oxo-1,3,2-dioxaphospholane, tetrahydrofuran (THF), chloroform, diethyl ether, methanol, and ethanol. All the chemicals were purchased from Sigma-Aldrich.

Evaluation of Monomer Hydrophilicity

The hydrophilicity of polymerisable UV absorbers was assessed by mixing a selected UV absorbing monomer in an aqueous solution containing 42% HEMA (58% water). Precipitation of the UV absorbing monomer indicates that the monomer is not sufficiently hydrophilic and could lead to formation of ocular lenses with reduced optical transparency.

Ocular Lens Characterisation

Equilibrium Water Content (EWC)

EWC was calculated from the sample's wet mass ($M_{wet}$, surface dried with lint-free wipes) and dry mass ($M_{dry}$, following drying at 40° C. overnight in a vacuum oven) according to Equation 1. The mass of a sample may be measured in grams (g). The average (ave) of at least 3 measurements was reported along with the standard deviation (s.d.).

$$EWC = \frac{M_{wet} - M_{dry}}{M_{wet}} \times 100\% \qquad \text{(Equation 1)}$$

For comparison, the difference in EWC values (ΔWC %) between a blank sample containing no UV absorber ($EWC_{Blank}$) and the UV-absorber containing sample ($EWC_{sample}$) is determined according to the following Equation 2:

$$\Delta WC\% = EWC_{Blank} - EWC_{sample} \qquad \text{(Equation 2)}$$

Optical Transparency

The optical transparency or visual appearance of the hydrogels was assessed by eye. Photographic images were also taken of the hydrogels on text to indicate levels of discolouration (yellowing) and optical haze. Optical transparency was also quantiatively assessed by visible light transmittance of the hydrogel or ocular lenses using UV-visible spectroscopy. At least five hydrogels containing the same concentration of UV absorbers within a same manufacturing batch were measured to give the average transmittance. T % was calculated as the average of light transmittance between 400 and 500 nm from a minimum of 5 samples.

For comparison, the difference in T % values (ΔT %) between the blank sample (T % Blank) and the UV-absorber containing sample (T %$_{sample}$) is determined according to the following Equation 3:

$$\Delta T\% = T\%_{Blank} - T\%_{sample} \qquad \text{(Equation 3)}$$

UV Blocking Ability

The ability of the hydrogel to block radiation in the UV-A and UV-B range was assessed by measuring the UV-visible transmission spectra of hydrated hydrogel films as recorded using a Varian Carey 60 on a quartz plate.

UV-A (315-380 nm) and UV-B (280-315 nm) blocking performances were calculated separately from the transmission spectra using Equations 4 and 5:

$$UV-A\ \text{Blocking} = 100\% - \frac{\sum_{315}^{380} T\%_\lambda \times \lambda}{\sum_{315}^{380} \lambda} \qquad \text{(Equation 4)}$$

$$UV-B\ \text{Blocking} = 100\% - \frac{\sum_{280}^{315} T\%_\lambda \times \lambda}{\sum_{280}^{315} \lambda} \qquad \text{(Equation 5)}$$

Presence of Yellow Tint

The presence of yellow tint was determined though visual observation by placing a hydrogel sample on a piece of white paper. The yellow appearance of the hydrogel samples can be corroborated with visible light transmittance results. If a sample absorbs light above 400 nm, it will reduce the average light transmittance between 400 and 500 nm. The absorption of a significant amount of light in the wavelength range of from 400-500 nm can indicate the presence of yellow tint.

Polymerisable UV Absorbers with Hydroxyphenyl-Benzotriazole Moiety

Polymerisable UV absorbers having a hydroxyphenyl-benzotriazole UV absorbing moiety were prepared by modifying the compound 2-[3-(2H-Benzotriazol-2-yl)-4-hydroxyphenyl]ethyl methacrylate (HB7) (CAS: 96478-09-0).

Synthesis of Polymerisable UV Absorber with Hydroxyphenyl-Benzotriazole Moiety and a Saccharide Linker (HB7-SGlu-MA)

Benzotriazol-2-yl)-4-hydroxyphenyl]ethyl methacrylate (HB-7, CAS: 96478-09-0, 1 g, 3.71 mmol) in anhydrous dimethyl sulfoxide (DMSO) (5 ml). After solubilizing the components dimethyl phenyl phosphine (DMPP) (0.22 mL, 0.5 eq., 1.5 mmol) was added dropwise. The mixture was magnetically stirred at room temperature overnight. The next day the intermediate HB7-SGlu was precipitated directly in diethyl ether and concentrated by centrifugation. Successful reaction was indicated by the disappearance of the methacrylate peaks (6.0, 5.6 and 1.85 ppm) and the emergence of α-methyl ester at 1.1 ppm and the glycoside anomeric proton at 5.1 ppm. The intermediate HB7-SGlu was then purified by column chromatography, whereby under 5% methanol in dichloromethane the hydrolysed HB7 eluted the column and under 15% methanol in dichloromethane the product was isolated (1.12 g, yield: 67%).

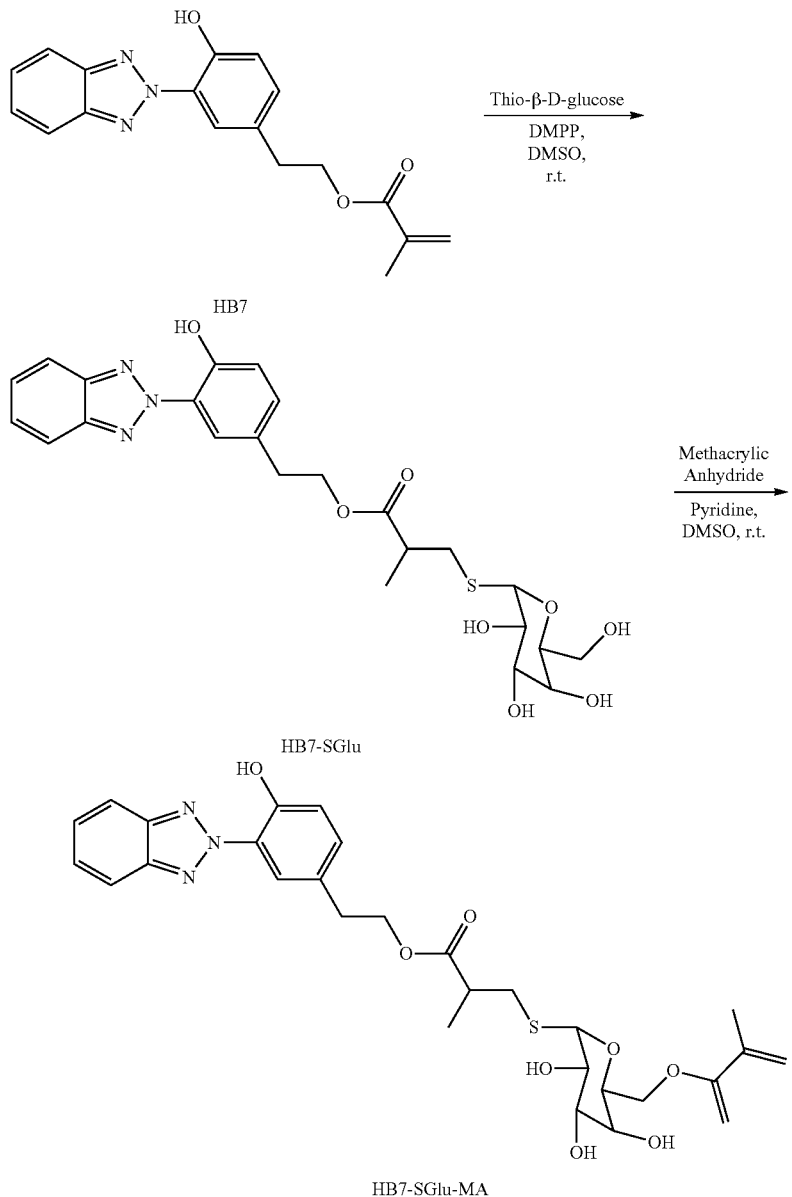

1-thio-β-D-glucose sodium salt (CAS: 10593-29-0, 0.81 g, 1.2 eq., 3.09 mmol) was added to a solution of 2-[3-(2H-

In the next step the resulting intermediate HB7-SGlu (0.55 g, 1.02 mmol) was dissolved in anhydrous DMSO (20 mL) in the presence of pyridine (0.2 mL, 2.0 eq., 2.0 mmol). Methacrylic anhydride (CAS: 760-93-0, 0.19 g, 1.2 eq., 1.22 mmol) was added subsequently to the reaction mixture. The emergence of methacrylate peaks at 6.1 and 5.8 ppm indicated successful re-attachment of the polymerisable group to the cysteine moiety. For purification the reaction mixture was added to diethyl ether to precipitate the crude product. The resultant product HB7-SGlu-MA was purified using column chromatography (15% v/v methanol in dichloromethane) to give about 0.37 g white-off solid (yield: 61%). The ESI-MS showed a mass of 610.1875 m/z (+Na). The attachment of thioglucose allowed the polymerisable UV absorber to exhibit a sugar moiety in its linker. HB7-SGlu-MA was also found to be soluble in D20.

Synthesis of Polymerisable UV Absorber with Hydroxyphenyl-Benzotriazole Moiety and an Anionic Linker (HB7-Cys-MA)

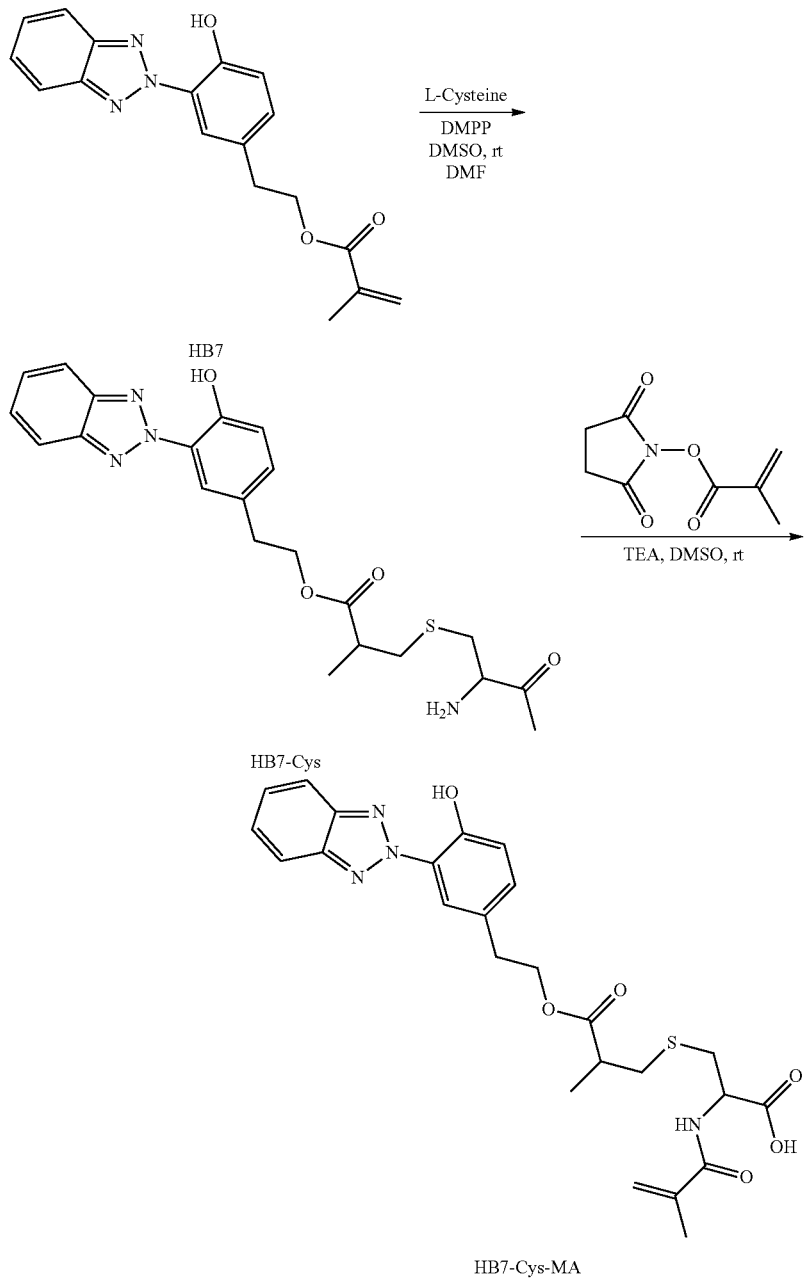

L-Cysteine.HCL (7.3 g, 1.5 eq., 46.4 mmol) was added to a solution of 2-[3-(2H-Benzotriazol-2-yl)-4-hydroxyphenyl] ethyl methacrylate or HB-7 (CAS: 96478-09-0, 10 g, 30.92 mmol) in DMSO (60 ml) and N,N.-dimethylformamide (DMF) (60 mL) mixture. After solubilizing the components (sonication might be required to enhance L-cysteine solubility) DMPP or dimethyl phenyl phosphine (2.2 mL, 0.5 eq., 15.46 mmol) was added dropwise. The mixture was magnetically stirred at room temperature overnight. The next day the intermediate HB7-Cys precipitated from the solution, which was filtered using Buchner funnel under vacuum. The precipitate was washed with dichloromethane during the filtration process. Successful reaction was indicated by the disappearance of the methacrylate peaks (6.0, 5.6 and 1.85 ppm) and the emergence of α-methyl ester at 1.1 ppm. The intermediate HB7-Cys was then heated in ethanol under reflux for re-crystallization to give 12 g of yellowish solid (yield: 87%).

The resulting intermediate HB7-Cys (3 g, 6.76 mmol) was dissolved in anhydrous DMSO (20 mL) in the presence of triethylamine (1.9 mL, 2.2 eq., 14.87 mmol). N-hydroxysuccinimidyl methacrylate or NHS-MA (CAS: 38862-25-8, 1.28 g, 1.2 eq., 8.12 mmol) was pre-dissolved in DMSO (3 mL) and added subsequently to the reaction mixture. Methacryloyl chloride could be used as an alternative to NHS-MA, however, side reaction would likely occur due to high reactivity of the reagent. The emergence of methacrylamide peaks at 5.7, 5.36 and 4.4 ppm indicated successful re-attachment of the polymerisable group to the cysteine moiety. The integration of the benzotriazole proton from HB-7 at 7.84 ppm (2 protons) compared to the methacrylamide proton at 5.30 ppm (1 proton) indicated that about 1:1 molar attachment of methacrylamide linker to the hydroxyphenyl-benzotriazole moiety. For purification the reaction mixture was diluted in DCM, followed by washing with water (brine solution can be added to break the emulsion). The organic phase was dried over $MgSO_4$, followed by solvent removal under vacuum. The resultant product HB7-Cys-MA was purified using column chromatography (15% v/v methanol in dichloromethane) to give about 1.8 g white-off solid (yield: 51%). The ESI-MS showed a mass of 511.1648 m/z (−H) and 535.1622 m/z (+Na). The attachment of cysteine allowed the polymerisable UV absorber to exhibit a carboxylic acid (anionic) group in its linker. HB7-Cys-MA was also found to be soluble in basic aqueous and brine solutions.

Synthesis of Polymerisable UV Absorber with Hydroxyphenyl-Benzotriazole Moiety and a Zwitterionic Linker (HB7-PC-MA)

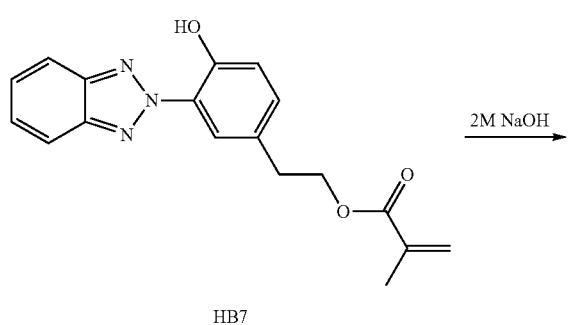

HB7

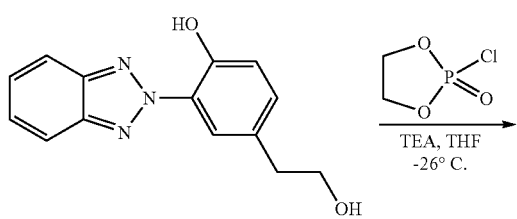

CAS: 36549-95-0
HB7-dE

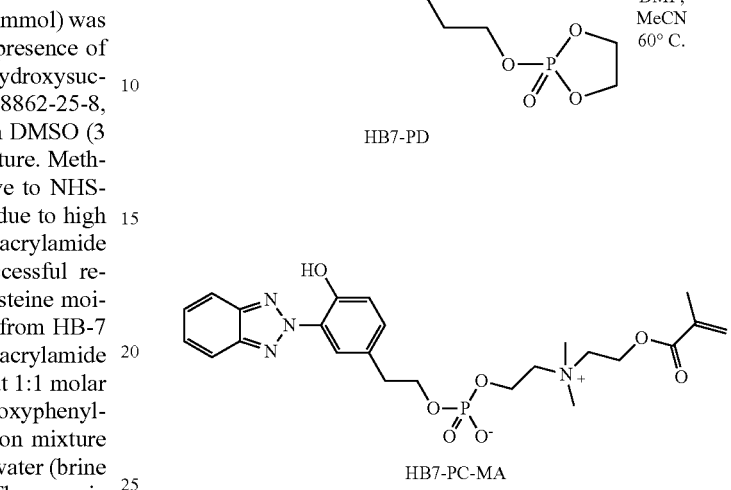

HB7-PD

HB7-PC-MA 10 g of 2-[3-(2H-Benzotriazol-2-yl)-4-hydroxyphenyl] ethyl methacrylate or HB-7 (CAS: 96478-09-0, 10 g, 30.92 mmol) was mixed with 200 mL of 2M sodium hydroxide (NaOH) solution. After one hour stirring, the pH was lowered to 1 with concentrated hydrochloric acid (HCl). A white product precipitated and was filtered off. The product was solubilised in dichloromethane and washed with water by liquid extraction for purification. After solvent removal, the hydrolysed HB-7 or HB7-dE (CAS: 96549-95-6) was dried for two days under vacuum.

2-chloro-2-oxo-1,3,2-dioxaphospholane (CAS: 6609-64-9, 1.01 g, 7.1 mmol) was dissolved in dry tetrahydrofuran (THF) (20 mL) and cooled to −25° C. Triethylamine (0.717 g, 7.1 mmol) was then added to the cold solution. The hydrolysed HB7 or HB7-dE (1.63 g, 6.4 mmol), was dissolved in dry THF (15 mL) and added dropwise to the phospholane solution over the course of 15 minutes. A further 5 mL of tetrahydrofuran was used to rinse the remainder of the HB7-dE into the flask. The mixture was stirred at −25° C. for 3 hours after which the triethylammonium salt was filtered off and the THF removed under vacuum to give a pale yellow oil. The crude product HB7-PD (2.55 g) was used without purification in the next step.

In the next reaction, the crude HB7-PD (2.55 g) was dissolved in dry acetonitrile (20 mL) and 2-(dimethylamino) ethyl methacrylate (DMAEMA) (CAS: 2867-47-2, 11.1 g, 10 eq.) was added. The reaction was stirred at 60° C. for 48 hours. The acetonitrile was removed under vacuum and excess DMAEMA was removed by decanting. The crude material was first dried overnight under high vacuum followed by stirring in ethanol overnight. The material was dialysed against ethanol using a 500 Da MWCO cellulose membrane. The product HB7-PC-MA (0.12 g) was obtained after solvent removal with 50% purity (unreacted HB7-PD was identified as the impurity). $^1$H-NMR confirmed the product through peaks at 4.5, 3.85 and 1.85 ppm, while $^{31}$P-NMR showed a shift from 18 to 0 ppm.

Synthesis of Polymerisable UV Absorber with Hydroxyphenyl-Benzotriazole Moiety and an Alternative Anionic Linker: HBE-Glu-MA

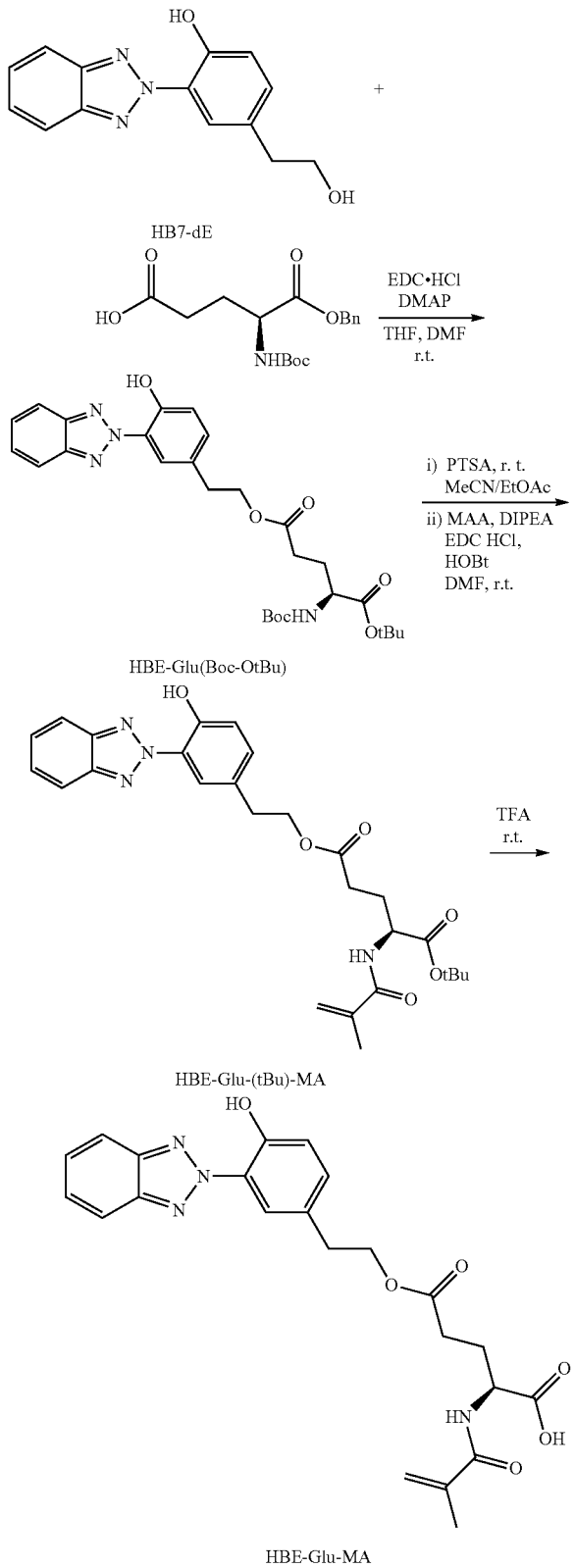

To anhydrous THF (200 mL) under nitrogen was added anhydrous DMF (100 mL), 2-(2H-benzo[d][1,2,3]triazol-2-yl)-4-(2-hydroxyethyl)phenol or HB7-dE (3.18 g, 12.5 mmol), (S)-5-(tert-butoxy)-4-((tert-butoxycarbonyl)amino)-5-oxopentanoic acid (8.70 g, 28.7 mmol), N-(3-dimethylaminopropyl)-N'-ethylcarbodiimide hydrochloride (EDC.HCl, 5.50 g, 28.7 mmol) and 4-dimethylaminopyridine (DMAP, 3.66 g, 29.9 mmol). The reaction was stirred at room temperature for 24 hours and then concentrated to remove the THF. The mixture was diluted with ethyl acetate (EtOAc) and water and separated. The aqueous phase was re-extracted (EtOAc) and the combined organics were washed with water, 0.5 M HCl, sat. $NaHCO_3$ solution and brine. The organic layers were then dried over $MgSO_4$ and reduced to a gum (9.9 g) under vacuum. The gum was taken up into anhydrous DMF (100 mL) under nitrogen and ammonium bicarbonate (4.93 g, 62 mmol) was added. The reaction was stirred at room temperature for 18 hours after which it was diluted with EtOAc and water and separated. The aqueous phase was re-extracted (EtOAc) and the combined organics were washed with water (2×) and brine. The organic layers were then dried over $MgSO_4$ and concentrated to give a white solid. The solid was recrystallised (MeCN) to give 5-(3-(2H-benzo[d][1,2,3]triazol-2-yl)-4-hydroxyphenethyl) 1-(tert-butyl) (tert-butoxycarbonyl)-L-glutamate or HBE-Glu(Boc-tBu) as colourless prisms (4.85 g, 72%). LCMS: $t_R$ 4.20 min, 95.1%, m/z 441.40 [(M+H)–Boc]$^+$. Succesful conjugation was indicated by the appearance ester peak at 4.32 ppm with corresponding aromatic peaks and protecting group peaks (Boc and tBu) at 1.40 ppm. at HBE-Glu(Boc-tBu) (2.00 g, 3.70 mmol) was subsequently added to a 4:1 mixture of acetonitrile and EtOAc (80:20 mL) under nitrogen was added p-toluenesulfonic acid (PTSA, 1.44 g, 7.59 mmol). The reaction was stirred at room temperature for 18 hours after which the precipitate was filtered off and washed with methyl tert-butyl ether (MTBE) to afford a white solid. The white solid was taken up into a mixture of sat. $NaHCO_3$ solution and EtOAc and separated. The aqueous phase was re-extracted (EtOAc) and the combined organics were washed with water (2×) and brine. The organic layers were then dried over $MgSO_4$ and concentrated to give an oil (1.6 g), presumably the amine, that was used without further purification. LCMS: $t_R$ 2.29 min, 90.15%, m/z 441.42 [(M+H)]$^+$. To anhydrous DMF (50 mL) under nitrogen was added methacrylic acid (MAA, 342 mg, 3.95 mmol), N,N-diisopropylamine (DIPEA, 1.50 mL, 8.62 mmol), EDC.HCl (826 mg, 4.31 mmol), hydroxybenzotriazole HOBt.20 wt % $H_2O$ (727 mg, 4.31 mmol) and, presumably, the amine from the previous step (1.58 g, 3.59 mmol) dissolved in DMF (20 mL). The reaction was stirred at room temperature for 18 hours after which it was diluted with EtOAc and water and separated. The aqueous phase was re-extracted (EtOAc) and the combined organics were washed with water (2×), 0.5 M HCl, sat. $NaHCO_3$ solution and brine. The organic layers were then dried over $MgSO_4$ and concentrated to give a white solid. This solid was purified by silica gel chromatography (EtOAc/petroleum ether 20:80) to afford a white solid (340 mg), presumably the methacrylamide tert-butylester HBE-Glu(tBu)-MA, that was used without further purification. LCMS: $t_R$ 3.76 min, 68.5%, m/z 453.36 [(M+H)–t–Bu]$^+$.

To the white solid, presumably the HBE-Glu(tBu)-MA (200 mg, ~70% pure), was added trifluoroacetic acid (4 mL). After 2.5 h the reaction was concentrated and the residue purified by silica gel chromatography (EtOAc/petroleum spirit 50:50, then, acetic acid/EtOAc 1:99) to afford (S)-5-(3-(2H-benzo[d][1,2,3]triazol-2-yl)-4-hydroxyphenethoxy)-

2-methacrylamido-5-oxopentanoic acid or HBE-Glu-MA as a white solid (115 mg). $^1$H-NMR confirmed the product through the hydroxyphenyl-benzotriazole (aromatic) peaks (7.0-8.22 ppm) with the polymerizable linker at 5.77, 5.37, 4.33 and 1.92 ppm. LCMS: $t_R$ 2.93 min, 99.57%, m/z 453.35 [(M+H)]$^+$.

Synthesis of Polymerisable UV Absorber with Hydroxyphenyl-Benzotriazole Moiety and an Alternative Anionic Linker: HBA-Lys-MA mL, 12.7 mmol), EDC.HCl (2.44 g, 12.7 mmol), HOBt.20 wt % H2O (1.72 g, 12.7 mmol) and methyl (tert-butoxycarbonyl)-L-lysinate—dissolved into 30 mL of anhydrous DMF—(3.14 g, 10.6 mmol). The reaction was stirred at room temperature for 18 hours after which it was quenched with 0.5 M HCl (100 mL). The organics were extracted with EtOAc (2×50 mL), washed with sat. NaHCO$_3$ solution (100 mL), water (100 mL) and brine (100 mL). The organic layers were then dried over MgSO$_4$ and reduced under vacuum to

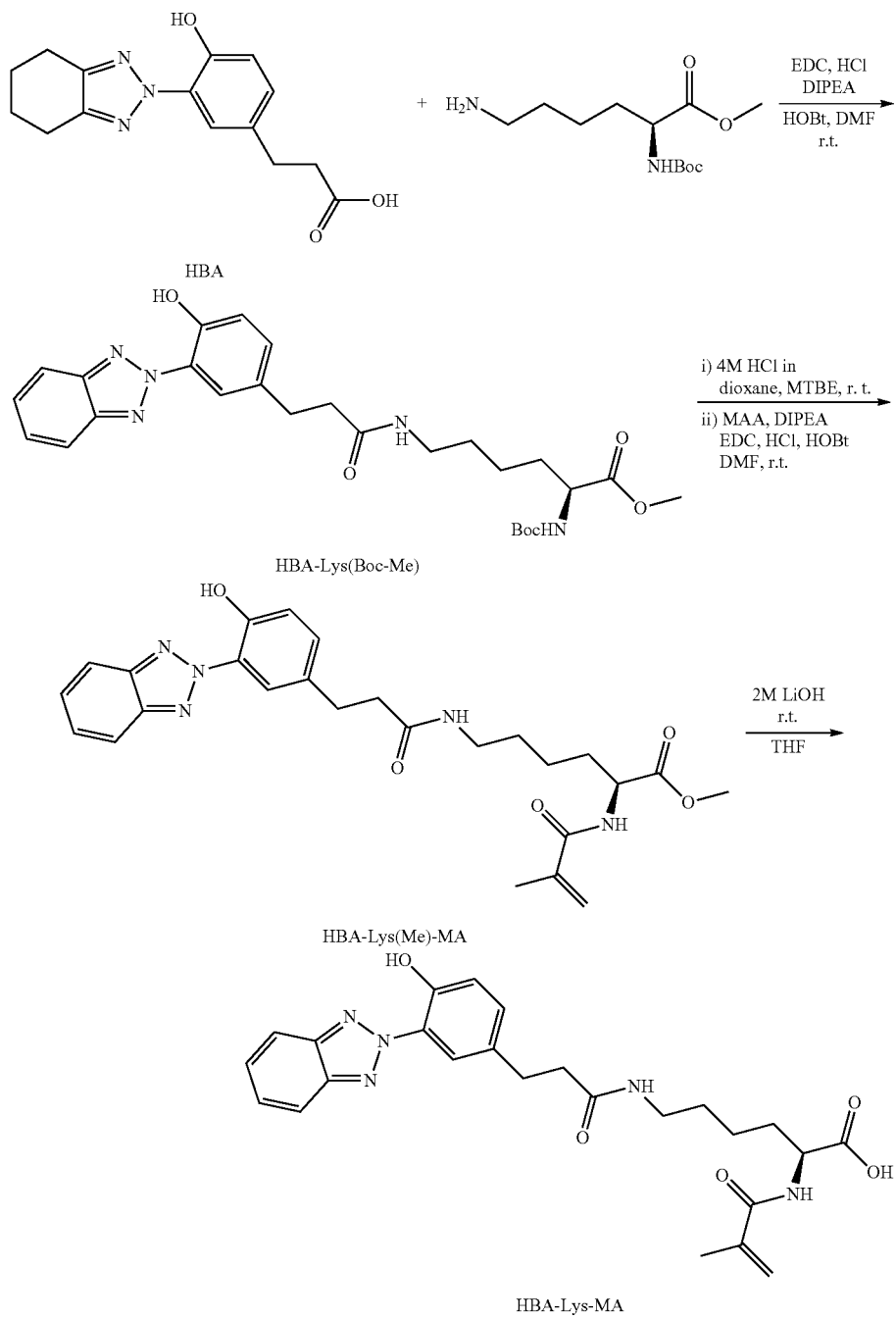

To anhydrous DMF (30 mL) under nitrogen was added 3-(3-(2H-benzo[d][1,2,3]triazol-2-yl)-4-hydroxyphenyl)propanoic acid or HBA (3.00 g, 10.6 mmol), DIPEA (2.21 give methyl N$^6$-(3-(3-(2H-benzo[d][1,2,3]triazol-2-yl)-4-hydroxyphenyl)propanoyl)-N$^2$-(tert-butoxy-carbonyl)-L-lysinate or HBA-Lys(Boc-Me). LCMS: $t_R$ 3.18 min, 95.1%, m/z 426.46 [(M+H)]⁺. Succesful conjugation was indicated by the appearance amide peak at 3.20 ppm with corresponding aromatic peaks and protecting group Boc peak at 1.56 ppm and methyl ester peak at 3.70 ppm. HBA-Lys(Boc-Me) (3.18 g, 6.05 mmol) was added to a mixture of MTBE (12 mL) and 4M HCl in dioxane (12 mL) under nitrogen. The reaction was stirred for 48 hrs after which the precipitate was filtered off and washed with diethyl ether (100 mL) to give the amine intermediate as an off-white powder (2.75 g, 98.6%). LCMS: $t_R$3.18 min, 95.1%, m/z 426.46 [(M+H)]⁺. Methyl N⁶-(3-(3-(2H-benzo[d][1,2,3]triazol-2-yl)-4-hydroxyphenyl)propanoyl)-L-lysinate hydrochloride (2.50 g, 5.41 mmol) was added to anhydrous DMF (80 mL) under nitrogen, followed by methacrylic acid (512 mg, 5.95 mmol), DIPEA (3.4 mL, 19.5 mmol), EDC.HCl (1.24 g, 6.49 mmol) and HOBt.20 wt % H2O (1.10 g, 6.49 mmol). The reaction was stirred at room temperature for 18 hours after which it was quenched with water (100 mL). The organics were extracted with EtOAc (2×50 mL), washed with 0.5M HCl (100 mL), sat. NaHCO₃ solution (100 mL), water (100 mL) and brine (100 mL). The organic layers were then dried over MgSO₄ and reduced under vacuum to give the product as an off-white powder. This was dissolved into anhydrous DMF (100 mL) under nitrogen, ammonium bicarbonate (1.00 g, 12.6 mmol) was added and the reaction stirred for 18 hrs. The reaction was quenched with water (100 mL), the organics were extracted with EtOAc (2×50 mL), washed with 0.5M HCl (100 mL), sat. NaHCO₃ solution (100 mL), water (100 mL) and brine (100 mL). The organic layers were then dried over MgSO₄ and reduced under vacuum to give the product HBA-Lys(Me)-MA as an off-white powder (1.75 g, 65.5%). LCMS: $t_R$ 2.81 min, 96.2%, m/z 492.38 [(M+H)]⁺.

To THF (15 mL) under ambient atmosphere was added methyl N-(3-(3-(2H-benzo[d][1,2,3]triazol-2-yl)-4-hydroxyphenyl)propanoyl)-N²-methacryloyl-L-lysinate or HBA-Lys(Me)-MA (193 mg, 0.391 mmol) followed by 2M LiOH (10 mL). The reaction was stirred for 18 hrs at room temperature after which it was quenched with 1M HCl to pH 5. The organics were extracted with EtOAc (2×25 mL) and washed with water (50 mL) and brine (50 mL), dried over MgSO₄ and reduced under vacuum to a solid. This was dissolved into 1M NaOH (25 mL), washed with EtOAc (2×25 mL) and acidified with 1M HCl to pH 5. The organics were extracted with EtOAc (2×25 mL), washed with 0.5M HCl (50 mL), sat. NaHCO₃ solution (50 mL), water (50 mL) and brine (50 mL). The organic layers were then dried over MgSO₄ and reduced under vacuum to give the product as an off-white powder HBA-Lys-MA (142 mg, 76.0%). ¹H-NMR confirmed the product through the hydroxyphenyl-benzotriazole (aromatic) peaks (7.08-8.03 ppm) with the polymerizable linker at 5.71, 5.36, 4.18, 3.01 and 1.86 ppm. LCMS: $t_R$ 2.54 min, 95.1%, m/z 480.4 [(M+H)]⁺.

Polymerisable UV Absorbers with Hydroxyl-Benzophenone Moiety

The compound 2-(4-benzoyl-3-hydroxyphenoxy)ethyl acrylate or BP15 (CAS: 16432-81-8). was derivatised to introduce a hydrophilic non-polyalkylene glycol linker.

Synthesis of Polymerisable UV Absorber with Hydroxyphenyl-Benzophenone Moiety and an Anionic Linker (BP15-Cys-MA)

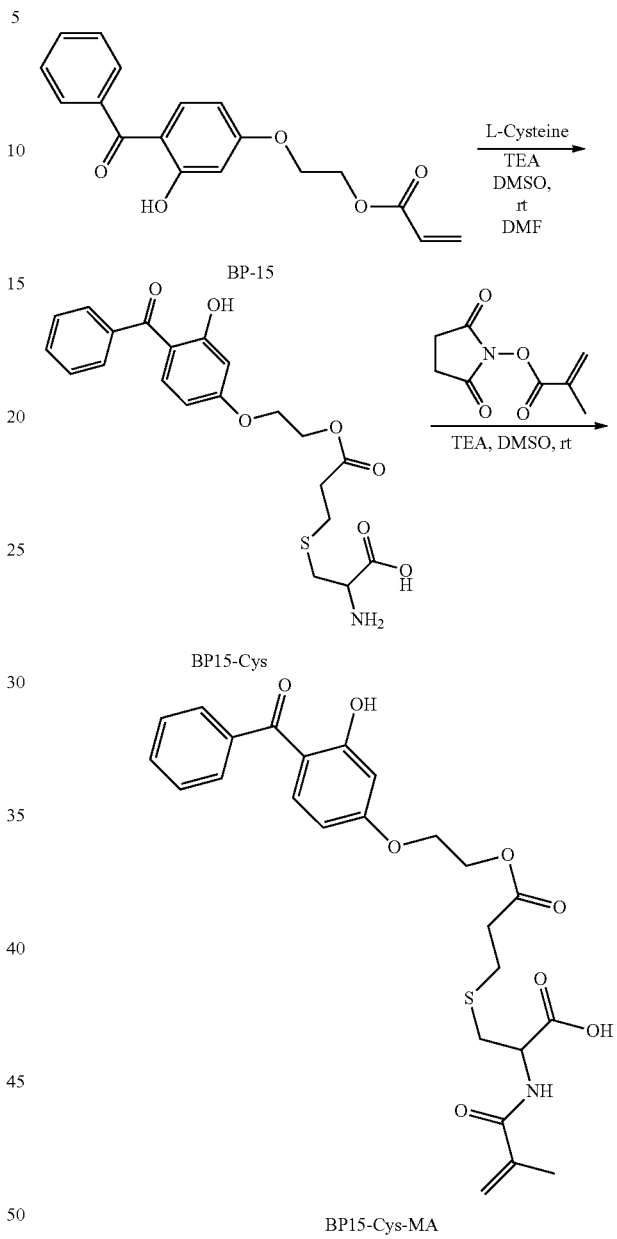

L-Cysteine.HCl (2.26 g, 1.5 eq., 14.4 mmol) was added to a solution of 2-(4-benzoyl-3-hydroxyphenoxy)ethyl acrylate (BP15, CAS: 16432-81-8, 3 g, 9.6 mmol) in DMSO (10 ml) and DMF (10 mL) mixture. After solubilizing the components (sonication might be required to enhance L-cysteine solubility) TEA or triethylamine (1.2 mL, 1.0 eq., 9.6 mmol) was added dropwise. The mixture was magnetically stirred at room temperature overnight. The next day the intermediate BP15-Cys precipitated from the solution, which was filtered using Buchner funnel under vacuum. The precipitate was washed with dichloromethane during the filtration process. Successful reaction was indicated by the disappearance of the acrylate peaks (6.0, 6.2 and 6.35 ppm).

The intermediate BP15-Cys was then heated in ethanol under reflux for re-crystallization to give 2 g of yellowish solid (yield: 48%). The resulting intermediate BP15-Cys (2 g, 4.61 mmol) was dissolved in anhydrous DMSO (15 mL) in the presence of triethylamine (1.3 mL, 2.2 eq., 1.01 mmol). N-hydroxysuccinimidyl methacrylate or NHS-MA (CAS: 38862-25-8, 1.1 g, 1.3 eq., 6.00 mmol) was pre-dissolved in DMSO (5 mL) and added subsequently to the reaction mixture. The emergence of methacrylamide peaks at 5.8, 5.3 and 4.4 ppm indicated successful re-attachment of the polymerisable group to the cysteine moiety. The integration of the benzophenone proton from BP15 at 6.47 ppm (1 proton) compared to the methacrylamide proton at 1.9 ppm (3 protons) indicated that about 1:1 molar attachment of methacrylamide linker to the benzophenone moiety. For purification the reaction mixture was diluted in DCM, followed by washing with water (brine solution can be added to break the emulsion). The organic phase was dried over MgSO$_4$, followed by solvent removal under vacuum. The resultant product BP15-Cys-MA was purified using column chromatography (15% v/v methanol in dichloromethane) to give about 0.6 g white yellowish solid (yield: 26%). The ESI-MS showed a mass of 500.138 m/z (−H) and 524.1356 m/z (+Na).

Synthesis of Polymerisable UV Absorber with Hydroxyphenyl-Benzophenone Moiety and a Zwitterionic Linker (BP15-PC-MA)

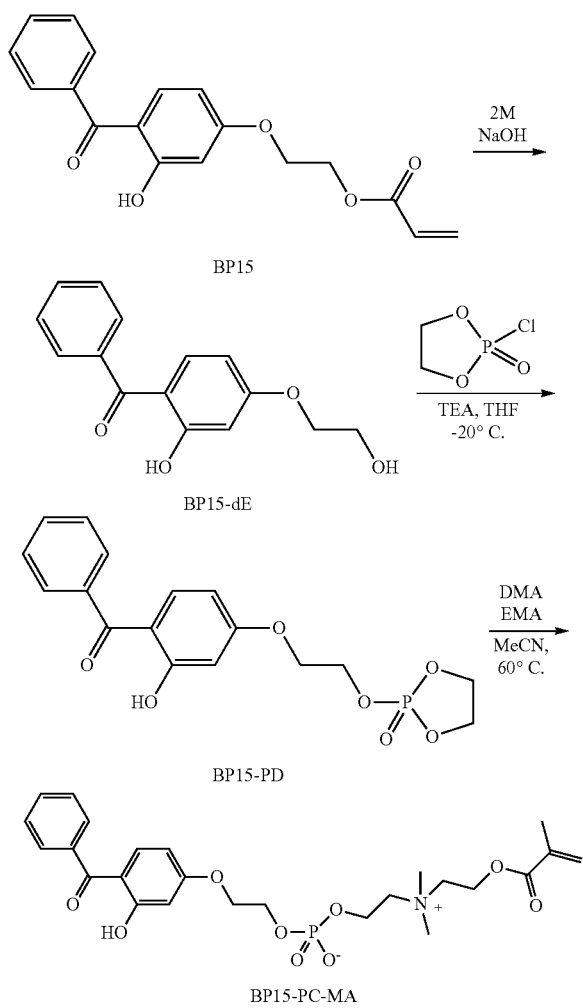

10 g of 2-(4-benzoyl-3-hydroxyphenoxy)ethyl acrylate or BP15 (CAS: 16432-81-8, 10 g, 38.7 mmol) was mixed with 200 mL of 2M sodium hydroxide (NaOH) solution. After one hour stirring, the pH was lowered to 1 with concentrated hydrochloric acid (HCl). A white product precipitated and was filtered off. The product was solubilised in dichloromethane and washed with water by liquid extraction for purification. After solvent removal, the hydrolysed BP15 or BP15-dE was dried for two days under vacuum.

2-chloro-2-oxo-1,3,2-dioxopholane (CAS: 6609-64-9, 1.02 g, 7.1 mmol) was dissolved in dry tetrahydrofuran (20 mL) and cooled to −25° C. Triethylamine (0.724 g, 7.1 mmol) was then added to the cold solution. Hydrolysed BP15 or BP15-dE (1.85 g, 7.1 mmol) was dissolved in dry tetrahydrofuran (15 mL) and added dropwise to the phospholane solution over the course of 15 minutes. A further 5 mL of tetrahydrofuran was used to rinse the remainder of the BP15-dE into the flask. The mixture was stirred at −25° C. for 3 hours after which the triethylammonium salt was filtered off and the tetrahydrofuran removed under vacuum to give a pale yellow oil. The crude product (2.65 g) was used without purification in the next step.

The crude BP15-PD (2.65 g, 7.3 mmol) was dissolved in dry acetonitrile (20 mL) and DMAEMA (CAS: 2867-47-2, 11.43 g, 10 eq.) was added. The reaction was stirred at 60° C. for 24 hours. The acetonitrile was removed under vacuum and excess DMAEMA was removed by decanting. The crude material was dissolved in chloroform and precipitated out in ether. This purification process was repeated two more times. The product BP15-PC-MA (0.35 g) was obtained after drying with 70% purity (unreacted BP15-PD was identified as the impurity). $^1$H-NMR confirmed the product through peaks at 4.6, 4.45, 4.0 and 1.9 ppm, while $^{31}$P-NMR showed a shift from 18 to 0 ppm.

General Method for Fabricating HEMA Hydrogels for Ocular Lenses:

Hydrogels incorporating the polymerisable UV absorbers, which are suitable for the manufacture of ocular lenses, were prepared according the following procedure:

Equipment

Polypropylene moulds (20 mm diameter, 0.1 mm height) with a 200 µL volume that can be filled with 214.8 mg of monomer mixture were used to prepare the hydrogels. Typically ten hydrogel samples were prepared for every formulation batch (total of 2148 mg for 10 times scale). The hydrogels formed in the moulds are typically flat samples having an average thickness of less than 200 µm.

Monomer Solutions

A bulk monomer mixture without AIBN was prepared as per Table 1 below. The monomers HEMA, MAA and TMPTMA were weighed out to the nearest 0.01 g and mixed using magnetic stirring (10 minutes). The bulk monomer mixture was stored in the fridge and used within 8 weeks.

TABLE 1

Composition of Bulk HEMA-based Monomer Mixture without AIBN

| | Molar mass (g/mol) | Wt % | Weight (g) | Density (g/ml) |
|---|---|---|---|---|
| HEMA | 130.14 | 96.5 | 48.25 | 1.074 |
| MAA | 86.09 | 3 | 1.5 | |
| TMPTMA | 338.4 | 0.5 | 0.25 | |

Hydrogel Preparation

To prepare hydrogel samples with different polymerisable UV absorbers (see Table 2), an amount of bulk monomer mixture as prepared above was weighed out into a vial then the desired UV blocker(s) added in the required amounts. AIBN (0.5 wt %) was then added to the monomer mixture containing the UV absorber prior to curing. A stirrer bar was added, the vial was sealed with a screw cap with septum, and the solution was mixed for 3 minutes using vortex mixer. Each sample was then purged by bubbling with argon gas using a needle into the solution for 10 minutes. If necessary, formulations containing the polymerisable UV absorbers were gently heated (i.e. 45° C.) to dissolve the components with visual checking for solubility every 30 sec.

Formulations with different polymerisable UV absorbers were then cast into polypropylene moulds using an electronic dispensing pipettor (200 ml per mould). Moulds were capped with a top half, clamped and the monomers polymerised under the following thermal conditions in a fan forced gas chromatography oven: 50° C. for 2 h, then ramped up to 90° C. and then maintained at 90° C. for 2 h. After polymerisation, the moulds were opened and the resultant polymer sample was immersed in 10% ethanol in PBS solution for 3-4 h. Subsequently the polymer samples were collected and hydrated individually in PBS solution at 37° C. overnight.

A control (blank) hydrogel sample was also prepared with a formulation containing the same mixture of hydrogel-forming monomers, but with no UV absorber.

Effect of Hydrophilic UV Absorber on HEMA-Based Hydrogel Water Content

The water content or EWC of the resultant hydrogel is an important parameter in ascertaining its suitability for use in an ocular lens. EWC results from some of the UV absorbing hydrogel samples of Table 2 are summarized in FIGS. 1 and 2 as change in water content (ΔWC %) relative to the blank hydrogel/base material.

The average EWC value determined for the blank HEMA-based hydrogel was 58.8±1.2%, which was calculated from 10 independent batches. Based on ±5% specification, the upper and lower limit of this blank hydrogel can be defined as 58.8±5%.

As shown in FIG. 1, hydrogels formed with HB7-Cys-MA (Example 1), HB7-PC-MA (Example 2) and HB7-SGlu-MA (Example 3 exhibited acceptable EWC values, which were within ±10% of the EWC of the blank sample. In particular, the HB7-Cys-MA containing hydrogel had EWC value of 57.7±1.1% (averaged from 5 batches), which resulted in ΔWC % of −1.2% relative to the blank.

Figure 2:
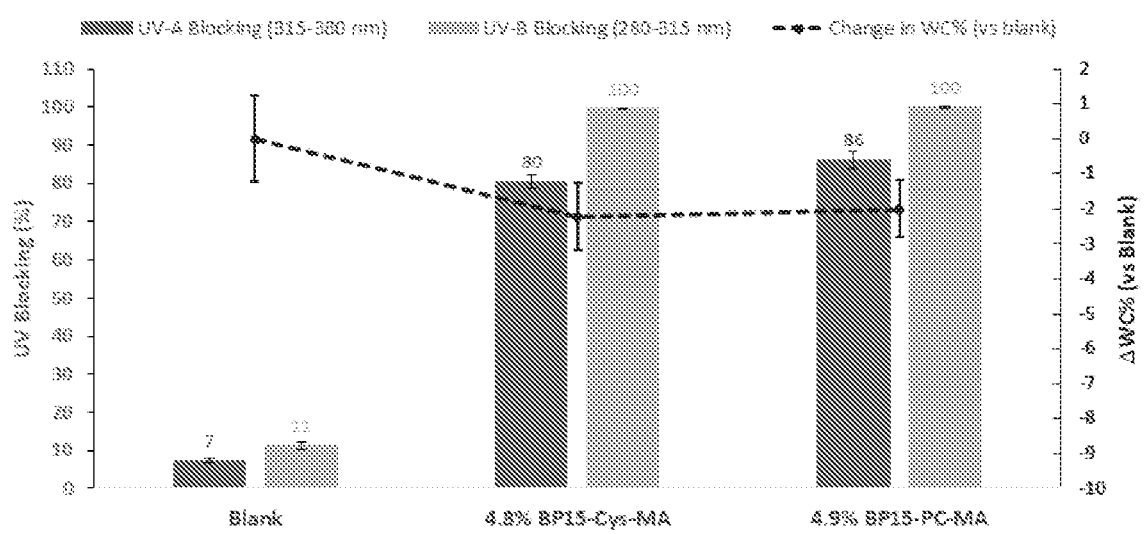
FIG. 2 is a graph illustrating the UV blocking performance and change in water content ($\Delta$WC % relative to the blank) results of hydrogel samples formed with polymerisable UV absorbers having a linker comprising an anionic, or zwitterionic moiety and a benzophenone UV absorbing moiety, compared to a blank hydrogel sample with no UV absorber.

As shown in FIG. 2, hydrogels formed with BP15-Cys-MA (Example 7) and BP15-PC-MA (Example 9) exhibited acceptable EWC values, which were within ±5% of the EWC of the blank sample. In particular, ΔWC % of the BP15-Cys-MA and BP15-PC-MA containing hydrogels resulted in about −2.0% relative to the blank.

TABLE 2

Formulations for preparing HEMA-based hydrogel samples (total volume 200 μL)

| Example No. | Formulation (w/w % UV absorber) | Weight of UV absorber (mg) | UV Absorber (mmol) | Weight of bulk HEMA-based monomer mixture (mg) |
|---|---|---|---|---|
| Blank | No UV absorber (control) | 0 | 0 | 214.8 |
| 1 | 4.8% HB7-Cys-MA | 10.23 | 0.02 | 214.8 |
| 2 | 4.9% HB7-PC-MA | 20.90 (50% pure) | 0.02 | 214.8 |
| 3 | 5.0% HB7-SGlu-MA | 11.75 | 0.02 | 214.8 |
| 4 | 4.4% HB7-Cys-MA | 9.46 | 0.0185 | 214.8 |
| 5 | 5.2% HB7-Cys-MA | 11.00 | 0.0215 | 214.8 |
| 6 | 3.6% HB7-Cys-MA/ 0.75% HB7 mixture (3:1) | 7.674 1.62 | 0.015 0.005 | 214.8 |
| 7 | 4.8% BP15-Cys-MA | 10.02 | 0.02 | 214.8 |
| 8 | 4.9% BP15-PC-MA | 14.90 (70% pure) | 0.02 | 214.8 |
| 9 | 1.55% HB7-Cys-MA/ 3.15% BP15-Cys-MA mixture (1:2) | 3.34 6.68 | 0.007 0.013 | 214.8 |

UV blocking performance and optical transparency of the different hydrogels was assessed.

Results on UV blocking performance for hydrogels of Examples 1 to 3, which are prepared with a hydroxyphenyl-benzotriazole UV absorbing moiety is shown in FIG. 1. It can be seen from FIG. 1 that the UV blocking performance of all the hydrogels containing HB7-Cys-MA (Example 1) and HB7-PC-MA (Example 2) in the UV-A and UV-B range could achieve ISO Class I UV blocking performance.

Results on UV blocking performance for some hydrogels of Examples 8 to 10, which are prepared with a hydroxyphenyl-benzophenone UV absorbing moiety is shown in FIG. 2. It can be seen from FIG. 2 that the UV blocking performance of hydrogels containing BP15-Cys-MA (Example 7), and BP15-PC-MA (Example 8) in the UV-A and UV-B range satisfy ISO Class II requirements.

Effect of Hydrophilic UV Absorber on HEMA-Based Hydrogel Optical Transparency

Figure 3:
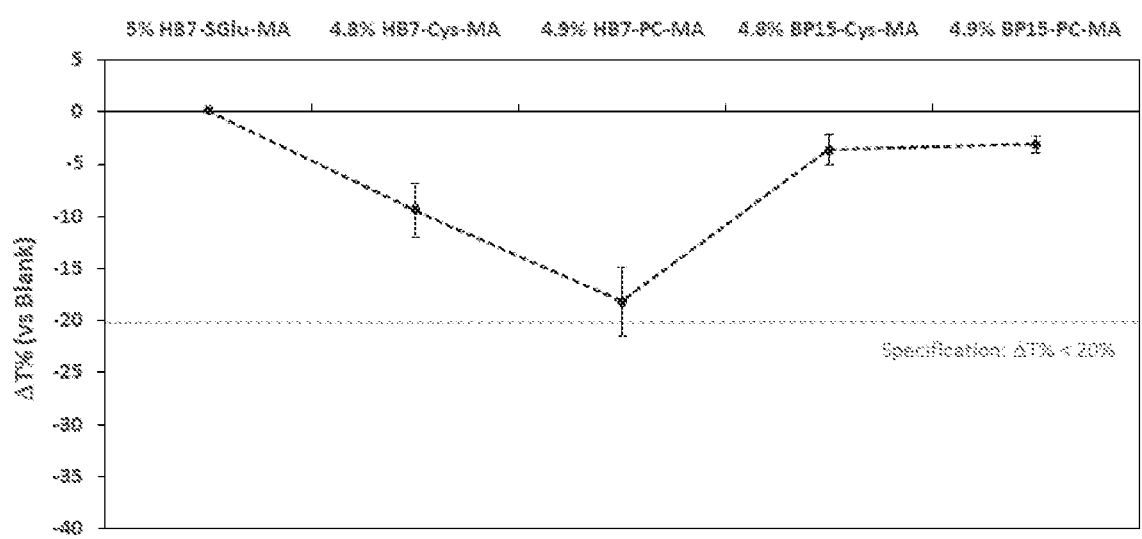
FIG. 3 is a graph illustrating the change in the average visible light (400-500 nm) transmittance ($\Delta$T % relative to the blank) results for hydrogel samples formed with the polymerisable UV absorbers having a linker comprising a saccharide an anionic, or zwitterionic linker and either a UV absorbing moiety (hydroxyphenyl-benzotriazole HB7 or benzophenone BP15).
Figure 4:
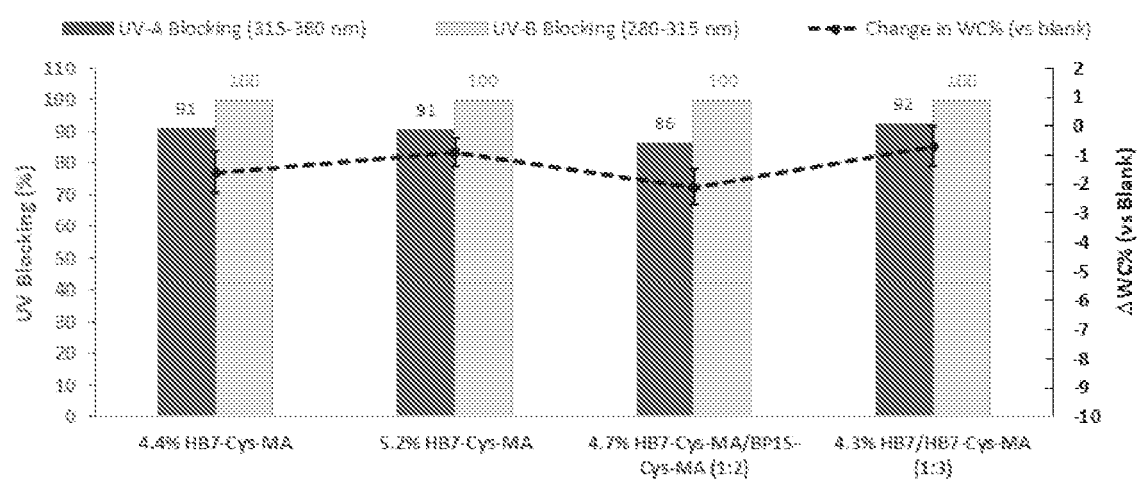
FIG. 4 is a graph illustrating the UV blocking performance and change in water content ($\Delta$WC % relative to the blank) results of hydrogel samples prepared with a polymerisable UV absorber having an anionic linker (HB7-Cys-MA) at different concentrations, and in admixture with another UV absorber (HB7 or BP15-Cys-MA).

Optical transparency assessment of the prepared hydrogel samples also showed that hydrogels formed with polymerisable UV absorbers having a charged or saccharide linker had excellent optical transparency. FIGS. 3 and 4 depict the change in average transmittance of the UV absorbing hydrogel samples relative to the blank/base material.

The HEMA-based blank hydrogel showed an average transmittance of about 98% within the 400-500 nm range.

As seen in FIG. 3, HEMA-based hydrogels prepared with HB7-Cys-MA (Example 1), HB7-PC-MA (Example 2) and HB7-SGlu-MA (Example 3) all exhibited excellent optical transparency and visible light transmission values, which were within acceptable limits. In particular, hydrogels prepared with HB7-Cys-MA exhibited an excellent optical transparency (T %) of 88.7% (or ΔT % of −9.4 relative to the blank). The optical transparency of Example 2 can be further improved by reducing the concentration of HB7-PC-MA, as it exhibited higher UV blocking performance (99% UV-A) than expected at 4.9%. These results show that HB7 derivative monomers having a hydrophilic non-polyalkylene linker do not have an unacceptable effect on hydrogel optical transparency, but can help to produce UV absorbing hydrogels having a visible light transmittance close to the blank sample.

In the same FIG. 3, HEMA-based hydrogels prepared with BP15-Cys-MA (Example 7) and BP15-PC-MA (Example 8) also exhibited excellent optical transparency and visible light transmission values, which were within acceptable limits. These results show that BP15 derivative monomers having a hydrophilic non-polyalkylene linker also have a positive effect on optical transparency and can help to produce UV absorbing hydrogels having a visible light transmittance that is similar to the blank sample.

Effect of Hydrophilic UV Absorber Concentration on HEMA-Based Hydrogel

Figure 5:
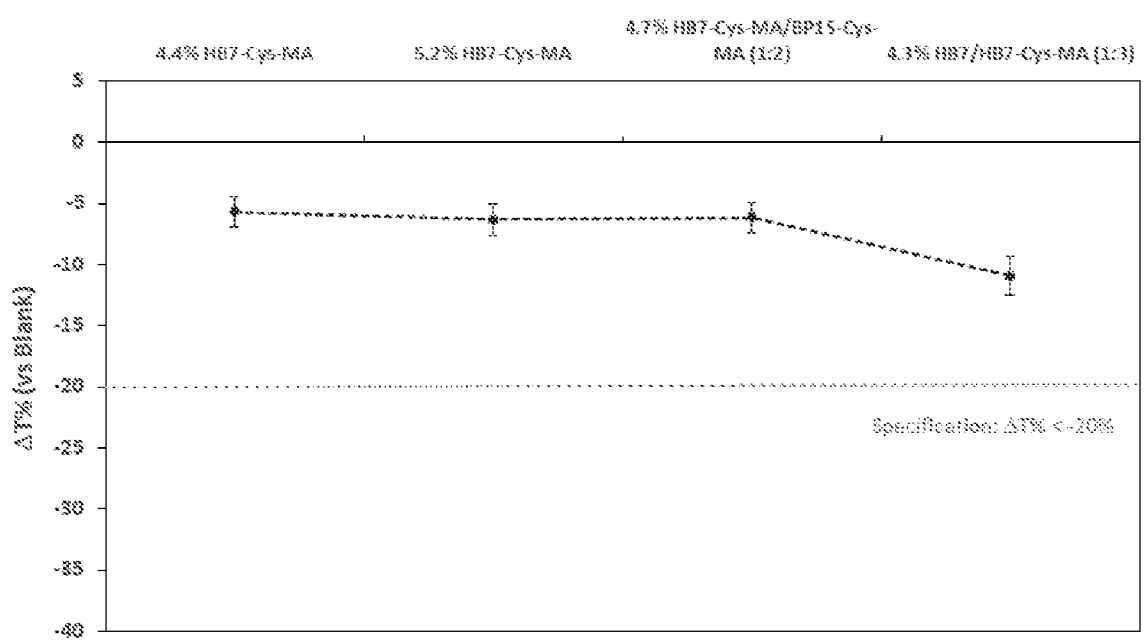
FIG. 5 is a graph illustrating the change in the average visible light (400-500 nm) transmittance ($\Delta$T % relative to the blank) of hydrogel samples prepared with a polymerisable UV absorber having an anionic linker (HB7-Cys-MA) at different concentration, and in admixture with another UV absorber (HB7 or BP15-Cys-MA), relative to a blank sample with no UV absorber.

Hydrogels containing two different concentrations of HB7-Cys-MA (4.4 wt % and 5.2 wt %) were assessed to determine how UV absorber concentration would effect the UV blocking performance and EWC of the hydrogel material. The hydrogel samples (Examples 4 and 5 in Table 2) were assessed for UV blocking performance, change in water content ($\Delta WC$ %) and optical transparency ($\Delta T$ %). The results are shown in FIGS. 4 and 5.

As seen in FIG. 4, the UV-visible blocking performance of hydrogels containing HB7-Cys-MA at concentrations of 4.4 wt % and 5.2 wt % were similar. Further, the EWC measurements show that an acceptable $\Delta WC$ % can be achieved at the different HB7-Cys-MA concentrations. Even at a higher concentration (5.2 wt %, Example 5), high EWC was still unexpectedly obtained for the HB7-Cys-MA containing hydrogel, which was within acceptable $\Delta WC$ % limits. Moreover, in an optical transparency assessment, it was found that the optical transparency of the HB7-Cys-MA containing hydrogels was not affected by the concentration of HB7-Cys-MA used (FIG. 5).

Mixture of UV Absorbers in HEMA-Based Hydrogel

A mixture of UV absorbers in the hydrogel was exemplified by mixing HB7-Cys-MA with either BP15-Cys-MA in a 1:2 ratio (Example 9 in Table 2) or the commercially available UV absorber HB7 in a 3:1 ratio (Example 6 in Table 2). The mixture was formulated to give a total UV absorber concentration of 0.02 mmol in the HEMA-based hydrogel, which corresponds to a total UV absorber concentration of 4.7 wt % and 4.3 wt % for the HB7-Cys-MA/BP15-Cys-MA and HB7/HB7-Cys-MA mixtures, respectively.

Results of UV blocking performance, $\Delta WC$ % and optical transparency for HEMA hydrogels prepared with the UV absorber mixtures are shown in FIGS. 4 and 5 as well. By mixing HB7-Cys-MA with BP15-Cys-MA (Example 9), the $\Delta WC$ % remained within acceptable limits and the EWC did not change significantly, compared to the hydrogels with HB7-Cys-MA alone. When HB7 and HB7-Cys-MA were incorporated in the hydrogel together a HB7-Cys-MA/HB7 3:1 molar ratio (Example 6), the EWC of the hydrogel unexpectedly improved (close to the blank). UV class I blocking performance was also achieved with the HB7-Cys-MA/HB7 containing hydrogel, while a high EWC was maintained (FIG. 4).

As seen in FIG. 5, HEMA-based hydrogels containing either a mixture of HB7-Cys-MA and BP15-Cys-MA (at a 1:2 molar ratio) or a mixture of HB7-Cys-MA and HB7 (at a 3:1 molar ratio) also exhibited high optical transparency, with $\Delta T$ % within acceptable limits, relative to the blank. This indicated that the hydrophilic anionic linker did not affect the hydrophilic environment of the hydrogel negatively, i.e. by precipitation that often leads to decrease in optical transparency.

Effect of Hydrophilic UV Absorber on Ionic Hydrogel

A proprietary mixture of monomers containing hydroxyethyl methacrylate (HEMA), dimethylaminoethyl chloride methacrylate, methacrylamidedimethylaminopropylmethyl chloride, 2-methacryloyloxyethylsuccinic acid, 2-methacryloyloxyethylhexahydrophtalic acid, and ethylene glycol dimethacrylate were prepared to provide an ionic (charged) hydrogel formulation. To this ionic hydrogel contact lens formulation (based on US 2012/0074352 patent), the required UV absorber was added, then the monomer mixture was cured thermally using AIBN to form the hydrogel polymer. The hydrogel preparation procedure described above for forming HEMA-based hydrogels was also used to prepare the ionic hydrogels.

Table 3 shows some examples of ionic hydrogel contact lens manufactured using this ionic formulation having different concentrations of HB7-Cys-MA and/or HB7. A control (blank) hydrogel sample was also prepared with a formulation containing the same mixture of hydrogel-forming monomers, but with no UV absorber.

TABLE 3

Formulation ratios for preparing ionic hydrogel samples (volume 200 µL)

| Formulation Example No. | Formulation (w/w % of UV absorber) | Weight of UV absorber (mg) | UV Absorber (mmol) | Weight of monomer mixture (mg) |
|---|---|---|---|---|
| Blank | No UV absorber | 0 | 0 | 500 |
| 10 | 1% HB7-Cys-MA | 5 | 0.010 | 500 |
| 11 | 2% HB7-Cys-MA | 10 | 0.020 | 500 |
| 12 | 3% HB7-Cys-MA | 15 | 0.029 | 500 |
| 13 | 3.2% HB7-Cys-MA | 16 | 0.031 | 500 |
| 14 | 3.5% HB7-Cys-MA | 17.5 | 0.034 | 500 |
| 15 | 4.0% HB7-Cys-MA | 20 | 0.039 | 500 |
| 16 | 4.5% HB7-Cys-MA | 22.5 | 0.044 | 500 |
| 17 | 2% HB7-Cys-MA/ 0.5% HB7 | 10 2.5 | 0.020 0.07 | 500 |
| 18 | 2% HB7-Cys-MA/ 1% HB7 | 10 5 | 0.020 0.015 | 500 |
| 19 | 1% HB7-Cys-MA/ 0.5% HB7 | 5 2.5 | 0.010 0.008 | 500 |
| 20 | 1% HB7-Cys-MA/ 1% HB7 | 5 5 | 0.010 0.015 | 500 |

The prepared ionic hydrogels were assessed for UV blocking performance and change in water content ($\Delta WC$ %).

While a blank HEMA-based hydrogel contact lens has EWC specification of 58±5%, this particular ionic hydrogel contact lens exhibited a EWC of 53% for the blank material. Accordingly, an EWC specification of 53±5% was set for the test ionic hydrogel samples, relative to the blank material.

Figure 6:
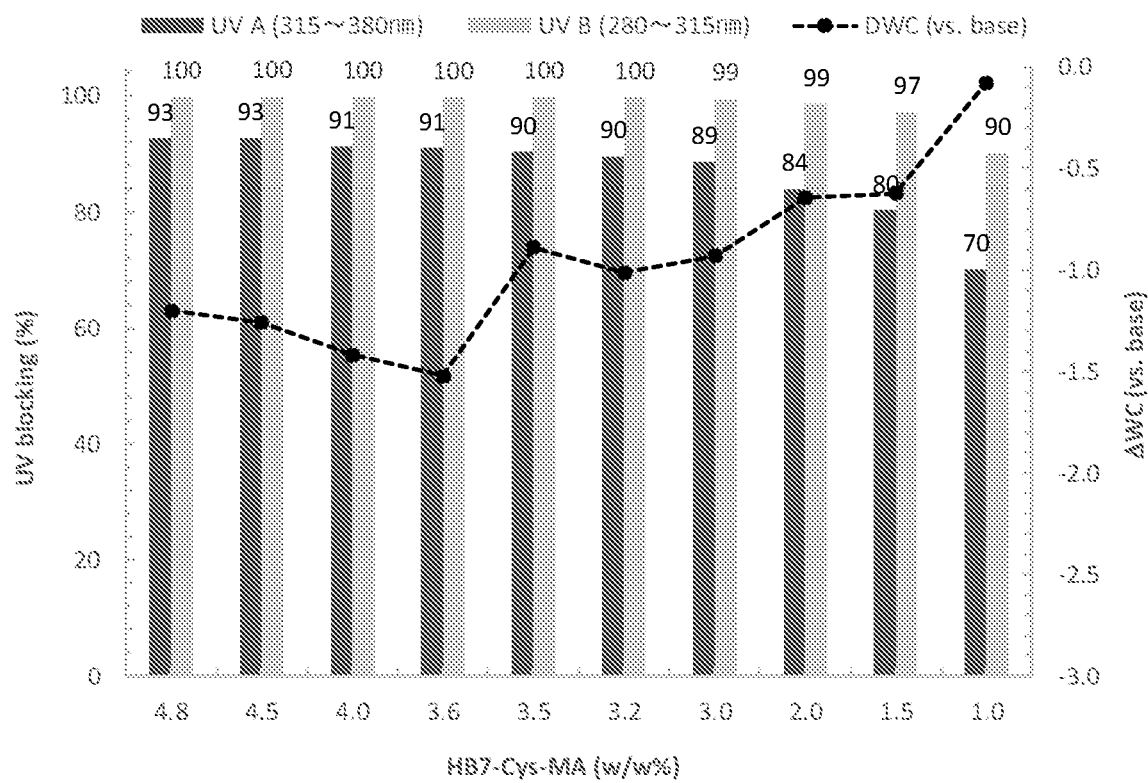
FIG. 6 is a graph illustrating the UV blocking performance and change in water content ($\Delta$WC % relative to the blank) results of ionic hydrogel samples prepared with a polymerisable UV absorber having an anionic linker (HB7-Cys-MA) at different concentrations.

FIG. 6 shows the effect of that various amounts of HB7-Cys-MA has on the UV blocking performance of this ionic hydrogel contact lens. At a concentration of 1.5 wt % HB7-Cys-MA, the contact lens was able to reach Class II UV blocking performance. The difference in EWC value ($\Delta$WC) between the UV-absorbing contact lens and the blank contact lens was displayed in FIG. 6 as well (Examples 1, and 10-16 as representative). $\Delta$WC % was maintained at <1.0% relative to the blank, when up to 3.5 w/w % HB7-Cys-MA was incorporated in the hydrogel. At higher HB7-Cys-MA concentrations the $\Delta$WC increased, however, the resultant EWC of the contact lens still meet the specification of 53±5% for the hydrogel contact lens.

Figure 7:
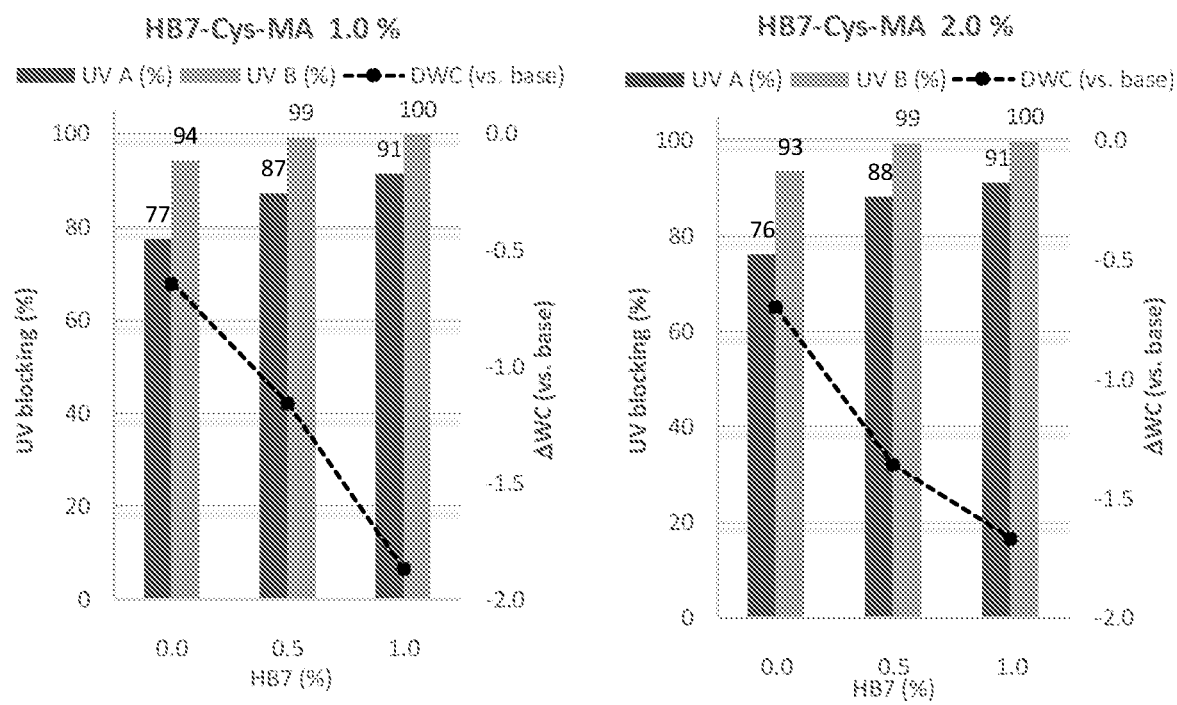
FIG. 7 is a graph illustrating the UV blocking performance and change in water content ($\Delta$WC % relative to the blank) results of ionic hydrogel samples prepared with a polymerisable UV absorber, having an anionic linker (HB7-Cys-MA) used at concentrations of 1.0 and 2.0% with a commercially available polymerisable UV absorber (HB7) at concentrations of of 0, 0.5 and 1.0%.

In contrast, the effect of HB7 on reducing the ionic hydrogel's EWC was significantly higher. FIG. 7 shows ionic hydrogel contact lenses containing a mixture of HB7-Cys-MA and HB7 at different ratios (Example 10, 11 and 17-20). Increasing the concentration of HB7 from 0 to 0.5 and 1.0 w/w % affected the EWC of the ionic hydrogel more significantly (i.e. a larger reduction in water content), in comparison with doubling the concentration of HB7-Cys-MA from 1.0 to 2.0 w/w %. The incorporation of HB7-Cys-MA in the ionic hydrogel improved the UV-visible transmission and optical transparency of these hydrogel contact lenses, when Class I UV blocking performance was met.

Summary of Test Hydrogel Results

Figure 8:
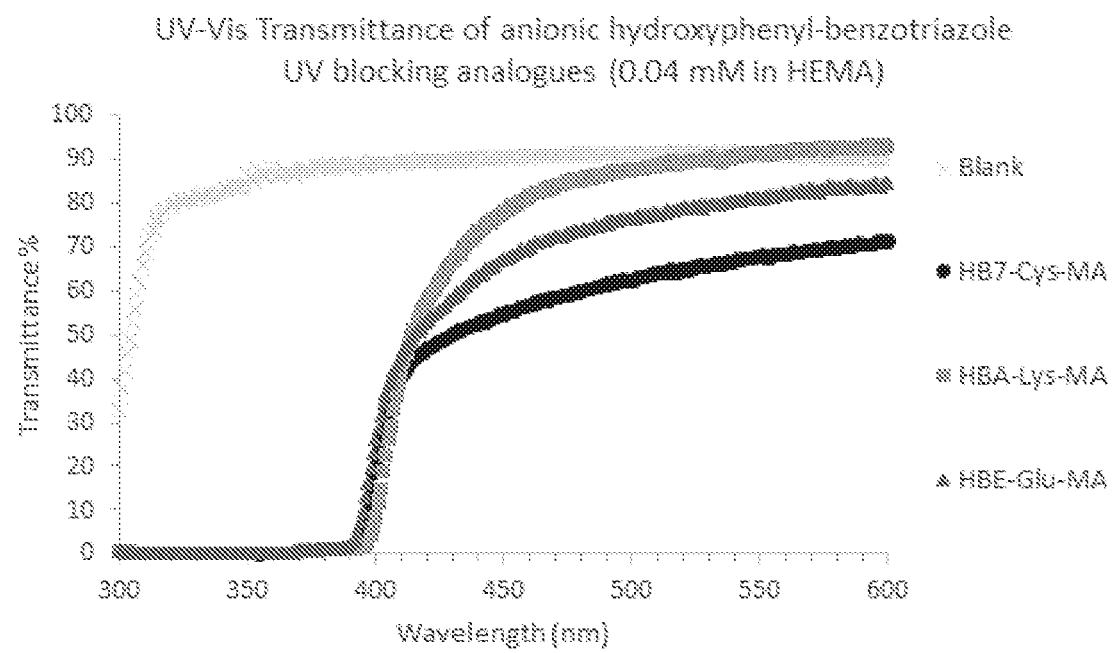
FIG. 8 is a graph illustrating the transmittance of UV blockers with anionic linkers (HB7-Cys-MA, HBE-Glu-MA, HBA-Lys-MA) at 0.04 mM concentration in hydroxyethyl methacrylate in comparison with a blank sample (no UV blocker).

A summary of results obtained from the evaluation of various HEMA and ionic hydrogels comprising different polymerisable UV absorbers is shown in Table 4. The various hydrogels were assessed to determine if they met the following performance criteria:

Change in water content ($\Delta$WC %)
  ○: Within ±5%. relative to the blank
  X: Outside ±5%, relative to the blank
UV blocking performance
  ○: Satisfy ISO Class II or more (UV-A blocking: >50%, UV-B blocking: >90%)
  X: Not satisfy ISO Class II
Optical Transparency reflected as change in the average 400-500 nm light transmittance ($\Delta$T %)
  ○: Reduction in transparency that is less than 20%, relative to the blank ($\Delta$T %<−20%)
  X: Reduction in transparency that is greater than 20%, relative to the blank ($\Delta$T %>−20%)
Yellow tint or yellowing
  ○: Not observable
  X: Observable The analogues of HB7-Cys-MA were also synthesized as additional examples of hydroxyphenyl-benzotriazole-based UV blocker with polymerizable anionic linker. FIG. 8 shows UV-Vis transmittance of HBE-Glu-MA and HBA-Lys-MA in comparison with HB7-Cys-MA at 0.04 mM concentration in HEMA as well as a blank sample (no UV blocker, HEMA only).

Comparative HEMA Hydrogel Examples

Comparative hydrogel samples were also made with comparative UV absorbers in which there is either (i) no linker, or (ii) a polyalkylene glycol linker connecting the UV absorbing moiety with the polymerisable moiety of the UV absorber. The comparative hydrogel samples were also prepared in the same manner as the test HEMA hydrogel samples of Table 2.

(i) Comparative Hydrogels with UV Absorber Containing No Linker

Comparative hydrogel samples were prepared with the industrially relevant reference UV absorber, HB7, either alone or as a mixture with another commercially available UV absorber, BP15. In the HB7 and BP15 UV absorbers, the UV absorbing moiety is directly linked to a polymerisable methacrylate group, such that there is no intermediate linker present in the monomers.

(ii) Comparative Hydrogels with UV Absorber Containing Polyalkylene Glycol Linker Comparative hydrogels were also prepared with UV absorbers having a polyethylene glycol (PEG) linker to connect a UV absorbing moiety to a polymerisable methacrylate group. The comparative PEG-containing absorbers are denoted as HB7-PEGMA and BP15-PEGMA.

As illustrated below, HB7-PEGMA was synthesised by (i) isolating the precursor $\alpha$-[3-[3-(2H-benzotriazol-2-yl)-5-(1,1-dimethylethyl)-4hydroxy-phenyl]-$\omega$-1-oxopropyl]-4-hydroxypoly(oxo-1,2-ethanediyl) from Tinuvin®1130, followed by methacrylation to provide HB7-PEGMA (scheme (a)).

TABLE 4

Representative results of UV-absorbing hydrogel samples

| Hydrogel Type | UV-absorber | Water Content | UV blocking Ability meeting ISO Class II | Optical Transparency | Yellow Tint |
|---|---|---|---|---|---|
| HEMA-MAA | 4.8% HB7-Cys-MA | ○ | ○ | ○ | ○ |
| | 5.0% HB7-SGluMA | ○ | ○ | ○ | ○ |
| | 4.8% BP15-Cys-MA | ○ | ○ | ○ | ○ |
| | 4.9% BP15-PC-MA | ○ | ○ | ○ | ○ |
| Ionic | 3.5% HB7-Cys-MA | ○ | ○ | ○ | ○ |

(a) Formation of HB7-PEGMA

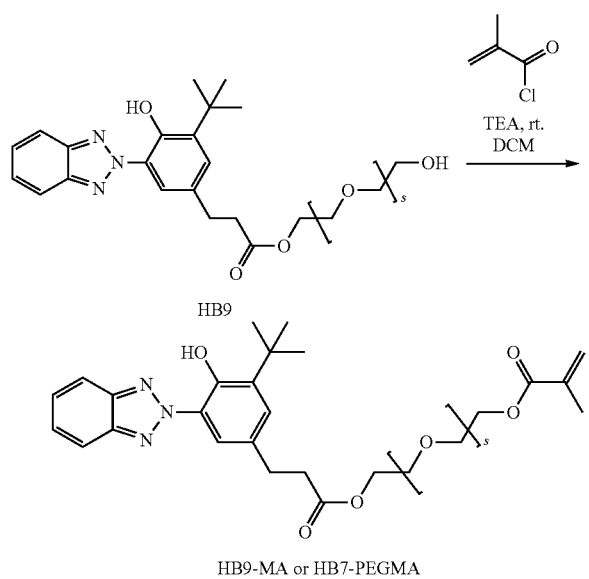

BP15-PEGMA was synthesised by conjugating BP15-dE with ω-(p-nitrophenyloxy)-poly(ethylene glycol) methacrylate or NPF-PEGMA. After purification the product BP15-PEGMA was obtained (scheme (b)).

(b) Formation of BP15-PEGMA

Comparative HEMA-based hydrogel samples were formed using the same hydrogel preparation protocol as that used to prepare the test HEMA hydrogel samples of Table 2. Similar concentrations of the comparative UV absorbers (on a molar basis) were used to prepare the comparative hydrogels. The formulations of the comparative hydrogels are shown in Table 5.

(iii) Comparative Hydrogels with UV Absorber Containing Cationic Linker

As illustrated below, HB7-DMAEMA was synthesized by conjugating the HB7-dE or 2-[3-(2H-Benzotriazol-2-yl)-4-hydroxyphenyl]ethanol with bromoacetylbromide, followed by the addition of 2-(dimethylamino)ethyl methacrylate or DMAEMA to provide a UV blocker with cationic or quaternary ammonium linker (scheme (c)).

(c) Formation of HB7-DMAEMA

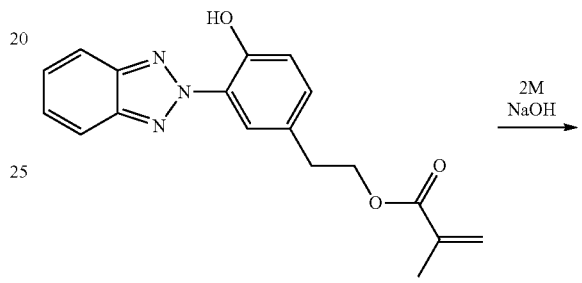

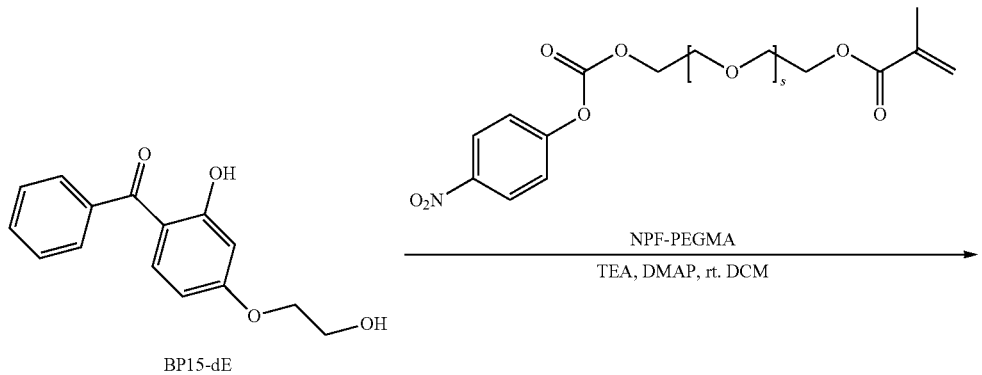

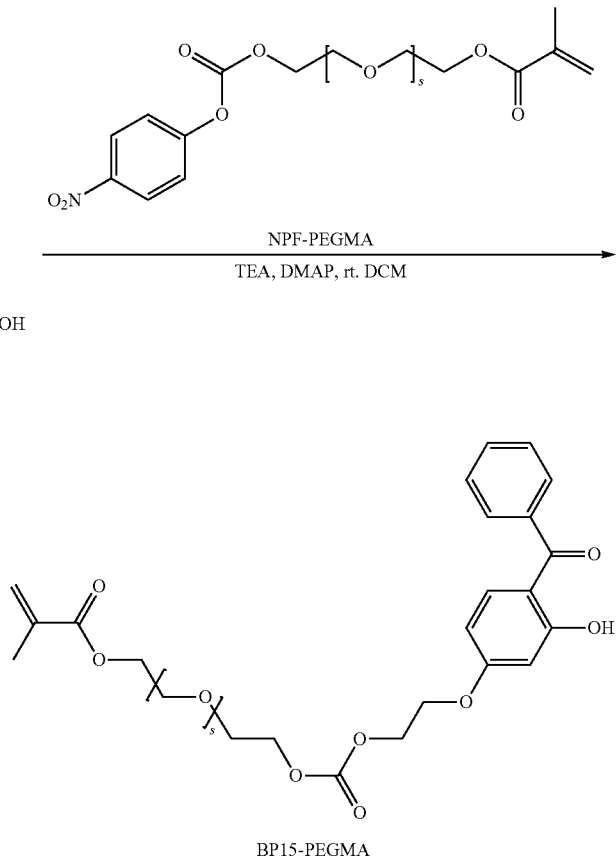

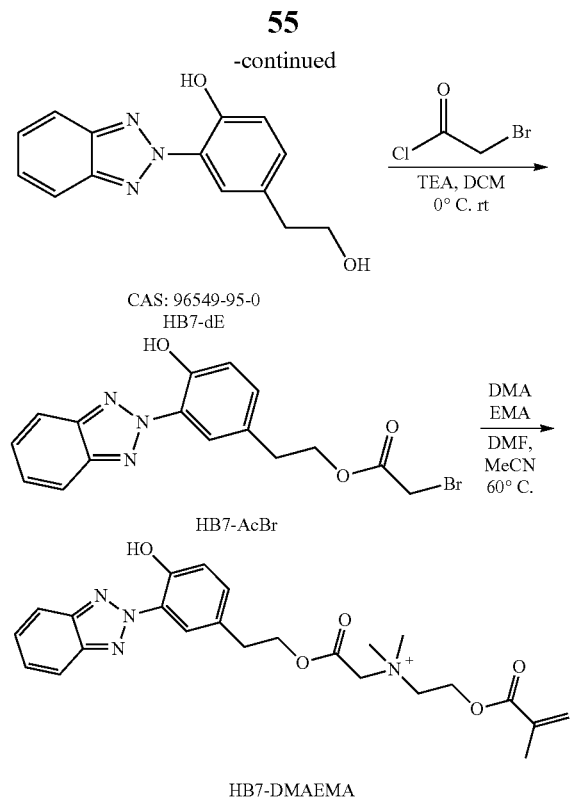

Cationic linker on BP15 can be synthesised through the same route as well by conjugating hydrolyzed BP15 (or BP15-dE) with bromoacetyl chloride, followed by the addition of DMAEMA.

TABLE 5

Formulations for preparing comparative HEMA-based hydrogel samples with comparative UV absorbers (total volume 200 μL)

| Comparative Example No | Formulation (w/w % UV absorber) | Weight of UV absorber (mg) | UV Absorber (mmol) | Weight of bulk HEMA-based monomer mixture (mg) |
|---|---|---|---|---|
| CE1 | 3% HB7 | 6.44 | 0.02 | 214.8 |
| CE2 | 1% HB7/2% BP15 mixture (1:2) | 2.16 4.16 | 0.007 0.013 | 214.8 |
| CE3 | 5% HB7-PEGMA (HB9-MA) | 10.74 | 0.016 | 214.8 |
| CE4 | 5% BP15-PEGMA | 10.74 | 0.014 | 214.8 |
| CE5 | 4.9% HB7-DMAEMA | 10.63 | 0.02 | 214.8 |

The comparative hydrogel samples were also assessed for water content (EWC), optical transparency (% T), UV blocking performance and presence of yellow tint, in accordance with the protocols described above.

Results

Figure 9:
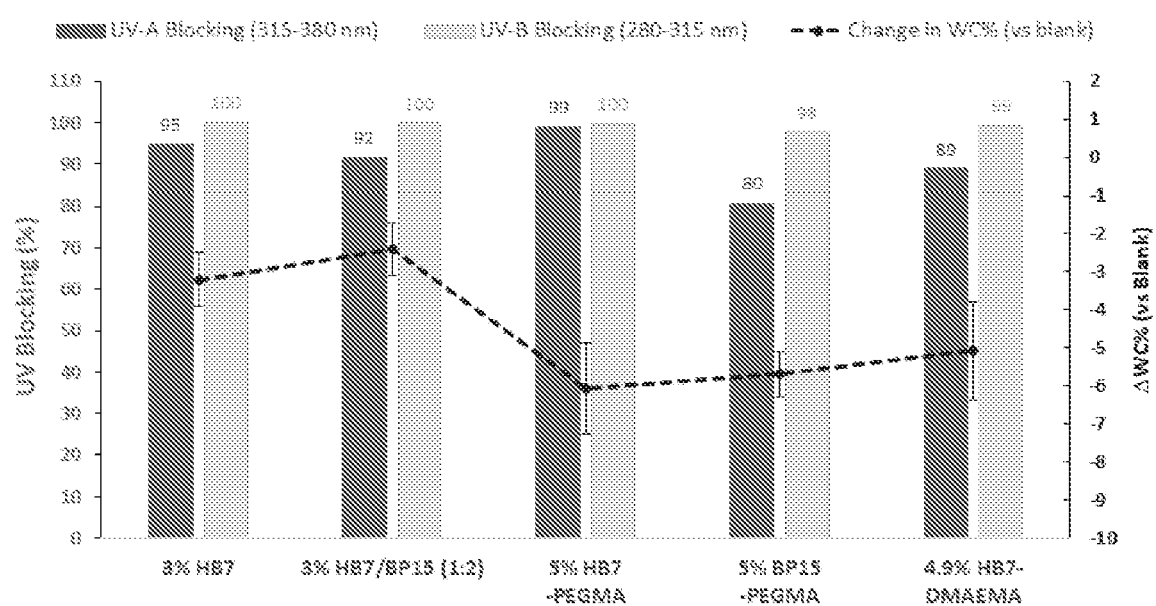
FIG. 9 is a graph illustrating the UV blocking performance and change in water content ($\Delta$WC % relative to the blank) results of comparative hydrogel samples (not of the invention), prepared with an industrially used UV absorber (HB7), a mixture of HB7 and another commercially available UV absorber (BP15), (neither of which have a hydrophilic non-polyalkylene glycol linker), UV absorbers containing a PEG linker (HB7-PEGMA and BP15-PEGMA), and UV absorbers containing a cationic linker (HB7-DMAEMA) at comparable concentrations to those used in the current invention.

The average EWC value from the comparative hydrogel sample containing 3% HB7 (CE1) was 55.5±1.1% from 7 batches (FIG. 9). This was lower than that obtained for a hydrogel of this invention, containing the anionic UV absorber BP15-Cys-MA (Example 8), which was able to obtain a higher EWC (56.7±1.0%) than CE1. The hydrogel formed with zwitterionic BP15-PC-MA UV absorber had an EWC of 56.9±0.8% and provided the second best result in this study due to higher UV-A blocking performance.

The comparative hydrogel sample containing 3% HB7 (CE1) showed low visible light transmittance and haziness (FIG. 10), as reflected by T % of 70.5% or ΔT % of −27.5% (out of specification) relative to the blank. In comparison with the invention, i.e. 4.8% HB7-Cys-MA (Example 1) improved significantly the EWC value of the HEMA-based hydrogel, with ΔWC % of −1.2% relative to the blank (FIG. 1). The optical transparency of HB7-Cys-MA containing HEMA-based hydrogel was maintained at a ΔT % value of around −6.9%, even at higher concentration up to 5.2% (FIGS. 3 and 5), which was not the case for HB7. By mixing HB7-Cys-MA with HB7 (3:1 molar ratio), Class I UV blocking HEMA-based hydrogel was also achieved with ΔWC % of −0.7% and ΔT % of −1.2% relative to the blank (FIGS. 4 and 5).

In ionic hydrogel HB7-Cys-MA at 3.5% w/w reached Class I UV blocking, while it changed slightly the water content of the blank (base material) by ΔWC % of −0.9% only (FIG. 6). In contrast, the effect of HB7 on reducing this ionic hydrogel's water content was significantly higher (Example 17-20). By using a mixture of HB7 and HB7-Cys-MA in ionic hydrogels, the effect of UV absorber's concentration can be observed on the EWC value of the hydrogel (FIG. 7). By increasing the concentration of HB7 by 0.5% the ΔWC % of −0.6% was achieved, while by increasing the concentration of HB7-Cys-MA by 1.0% the ΔWC % of −0.2% was achieved. Moreover it was difficult to maintain the solubility of HB7 in the monomer mixture, which often resulted in hazy contact lenses.

The comparison between a mixture of commercial UV absorbers, 3% HB7/BP15 at 1:2 molar ratio (CE2, FIG. 10), and a mixture of the UV absorbers with hydrophilic anionic linker (4.7% HB7-Cys-MA/BP15-Cys-MA at 1:2 molar ratio, FIG. 5) indicated that the optical transparency (ΔT % of −20.9% vs ΔT % of −6.1%) of the HEMA-based hydrogel can be significantly improved through the invention.

Comparative hydrogel samples CE3 and CE4 formed with a polymerisable UV absorber containing a polyethylene glycol (PEG) linker were also assessed against hydrogel samples prepared with commercially available HB7 alone (CE1) or a mixture of HB7 and BP15 (CE2). The prepared hydrogel samples were assessed for ability to block UV light, optical transparency and water content (EWC). Results on UV blocking performance and ΔWC % is shown in FIG. 9.

While BP15-PEGMA (CE4) has higher ethylene glycol content than HB7-PEGMA (CE3), it did not help to increase the water content of the hydrogel (FIG. 9). At similar a concentration to the HB7 and HB7/BP15 reference samples (CE1 and CE2), the 5 wt % HB7-PEGMA and 5 wt % BP15-PEGMA samples exhibited significantly lower EWC, and a greater ΔWC relative to the blank.

Figure 10:
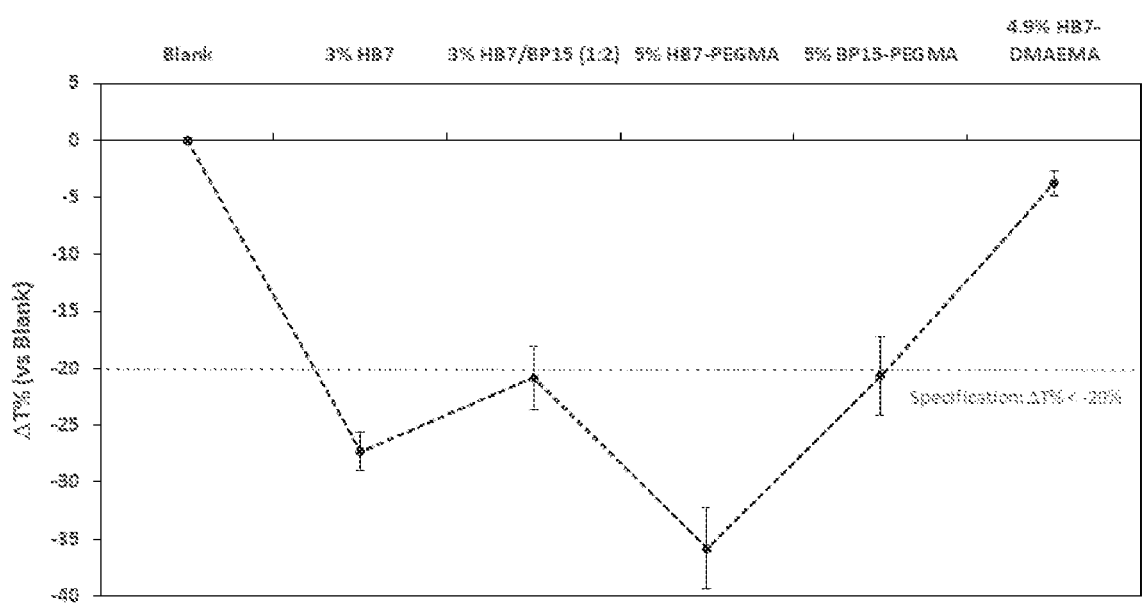
FIG. 10 is a graph illustrating the change in the average visible light (400-500 nm) transmittance ($\Delta$T % relative to the blank) results of hydrogel samples samples (not of the invention) prepared with an industrially used UV absorber (HB7), another commercially available UV absorber (BP15), (neither of which have a hydrophilic non-polyalkylene glycol linker), UV absorbers containing a PEG linker (HB7-PEGMA and BP15-PEGMA), and UV absorbers containing a cationic linker (HB7-DMAEMA) at comparable concentration to those used in the current invention.

Optical transparency assessment also showed that the hydrogel containing 3% HB7 exhibited low visible light transmittance and haziness, as reflected by T % of 70.5% or ΔT % of −27.5% (out of acceptable specification), relative to the blank. Furthermore, HEMA-based hydrogels containing HB7-PEGMA and BP15-PEGMA were not as good as the HB7 and HB7/BP15 samples. The resultant hydrogel samples containing HB7-PEGMA and BP15-PEGMA appeared to be opaque, and all comparative hydrogel samples exhibited ΔT % lower than ~20% relative to the blank/base material (FIG. 10).

A hydrophilic UV absorber with a cationic linker was represented with HB7-DMAEMA and incorporated into the HEMA-base hydrogel (CE5). As shown in FIG. 9, the cationic moiety reduced apparently the UV blocking performance of the UV absorber, requiring higher concentration of the compound to achieve the same performance as HB7-Cys-MA. However, even at 4.9% (the same molar concentration as HB7-Cys-MA) the EWC of the CE5 example was lower than expected (ΔWC slightly lower than −5%).

Comparative Ionic Hydrogel Example

A comparative ionic hydrogel sample was also made with the the industrially relevant reference UV absorber, HB7, in which the UV absorbing moiety is directly linked to a polymerisable methacrylate group, such that there is no intermediate linker present in the monomer. The comparative ionic hydrogel sample was also prepared in the same manner as the test ionic hydrogel samples of Table 3. The formulation of the comparative ionic hydrogel is shown in Table 6.

TABLE 6

Formulation for preparing comparative ionic hydrogel samples with comparative UV absorber (total volume 200 μL)

| Comparative Example No | Formulation (w/w % UV absorber) | Weight of UV absorber (mg) | UV Absorber (mmol) | Weight of monomer mixture (mg) |
|---|---|---|---|---|
| CE6 | 2.5% HB7 | 12.5 | 0.0375 | 500 |
| CE7 | 4.5% HB7-DMAEMA | 22.5 | 0.0423 | 500 |

The comparative ionic hydrogel sample was also assessed for water content (EWC), optical transparency (% T), UV blocking performance and presence of yellow tint, in accordance with the protocols described above.

The UV absorber with the cationic linker, HB7-DMAEMA, was also incorporated to the ionic hydrogel at 4.5 wt % (CE7) for comparison. While the same UV blocking performance could not be achieved as CE6 and the HB7-Cys-MA containing ionic hydrogel (Examples 14-16). Moreover, the optical transparency of the ionic hydrogel decreased in CE7 sample due to appearance of HB7-DMAEMA precipitate in the ionic hydrogel.

Results

At 2.5% HB7 class I UV blocking was achieved by the hydrogel sample. However, the EWC and optical transparency of the hydrogel decreased dramatically. HB7 did not appear to be soluble in the ionic hydrogel sample, as the solid HB7 precipitated after the hydration and autoclave processes of the contact lens.

Summary of Comparative Hydrogel Results

A summary of results obtained from evaluation of various comparative HEMA-based hydrogels comprising different comparative UV absorbers is shown in Table 7. The various hydrogels were assessed to determine if they met the following performance criteria:

Change in water content (ΔWC %)
○: Within ±5%, relative to the blank
X: Outside ±5%, relative to the blank UV blocking performance
○: Satisfy ISO Class II or more (UV-A blocking: >50%, UV-B blocking: >90%)
X: Not satisfy ISO Class II Optical Transparency reflected as change in the average 400-500 nm light transmittance (ΔT %)
○: Reduction in transparency that is less than 20%, relative to the blank (ΔT %<-20%)
X: Reduction in transparency that is greater than 20%, relative to the blank (ΔT %>-20%)

Yellow tint or yellowing
○: Not observable
X: Observable

TABLE 7

Results of comparative UV-absorbing hydrogel samples

| Hydrogel Type | Comparative UV absorber | Water Content | UV blocking Ability meeting ISO Class II | Optical Transparency | Yellow Tint |
|---|---|---|---|---|---|
| HEMA-MAA | 3.0% HB7 | ○ | ○ | x | x |
|  | 1.0% HB7/2.0% BP15 mixture | ○ | ○ | ○ | x |
|  | 5.0% HB7-PEGMA | ○ | ○ | x | x |
|  | 5.0% BP15-PEGMA | ○ | ○ | x | x |
|  | 4.9% HB7-DMAEMA | x | ○ | ○ | ○ |
| Ionic | 2.5% HB7 | ○ | ○ | x | x |
|  | 4.5% HB7-DMAEMA | ○ | ○ | x | x |

It is to be understood that various other modifications and/or alterations may be made without departing from the spirit of the present invention as outlined herein.

The invention claimed is:

1. An ocular lens comprising a hydrogel polymer comprising polymerised residues derived from a polymerisable UV absorber of formula (I):

U-L-Py      (I)

wherein:
U is a UV absorbing moiety;
L is a hydrophilic non-polyalkylene glycol linker comprising an anionic, a zwitterionic or a saccharide moiety; and
Py is an ethylenically unsaturated polymerisable moiety.

2. The ocular lens according to claim 1, wherein the linker (L) comprises at least 4 carbon atoms.

3. The ocular lens according to claim 1, wherein the linker (L) comprises a moiety selected from carboxylate, sulfonate, sulfate, phosphate, phosphonate, ammonium, and combinations thereof.

4. The ocular lens according to claim 1, wherein the linker (L) comprises a moiety selected from formulae (IIa), (IIb), (IIc), (IId) and (IIe):

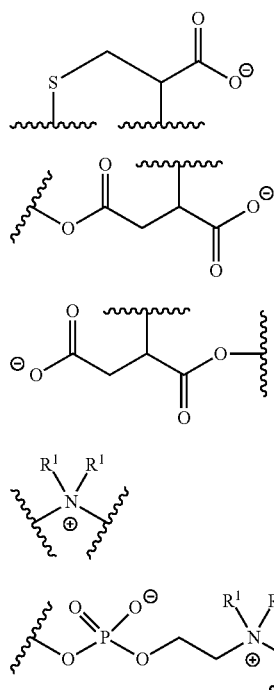

wherein $R^1$ at each occurrence is independently selected from H and $C_1$-$C_4$ alkyl, and ∼∼∼ represents the remainder of the polymerisable UV absorber of formula (I).

5. The ocular lens according to claim 1, wherein the linker (L) has a structure selected from formulae (IIIa), (IIIb), (IIIc), and (IIId):

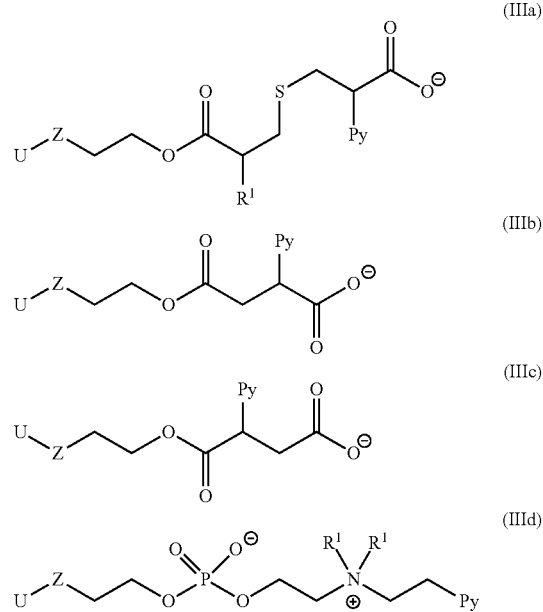

wherein:
$R^1$ at each occurrence is independently selected from H and $C_1$-$C_4$ alkyl;
Z is absent or is a heteroatom;
U is the UV absorbing moiety; and
Py is the ethylenically unsaturated polymerisable moiety.

6. The ocular lens according to claim 1, wherein the linker (L) comprises a saccharide moiety selected from a furanose, pyranose and amino sugar moiety.

7. The ocular lens according to claim 6, wherein the linker (L) comprises a glucopyranose or glucosamine moiety.

8. The ocular lens according to claim 6, wherein the linker (L) has a structure selected from formulae (Xa) and (Xb):

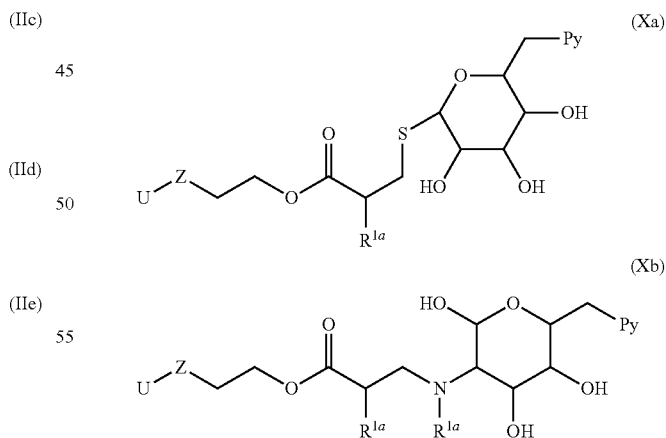

wherein in formula (Xa) and (Xb):
$R^{1a}$ at each occurrence is independently selected from H and $C_1$-$C_4$ alkyl;
Z is absent or is a heteroatom;
U is the UV absorbing moiety; and
Py is the ethylenically unsaturated polymerisable moiety.

9. The ocular lens according to claim 1, wherein the UV absorbing moiety (U) absorbs radiation in both the UV-A and UV-B range.

10. The ocular lens according to claim 1, wherein the UV absorbing moiety (U) is a benzotriazole or benzophenone moiety.

11. The ocular lens according to claim 10, wherein the UV absorbing moiety (U) has a structure of formula (IV):

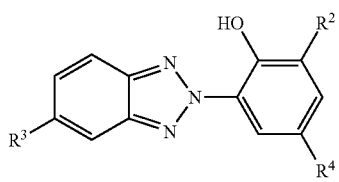

(IV)

wherein
$R^2$ is selected from the group H and $C_1$-$C_5$ alkyl;
$R^3$ or $R^4$ represents an attachment point to the linker (L), and wherein:
  if $R^3$ is the attachment point to the linker (L), then $R^4$ is selected from H, alkyl and alkoxy; or
  if $R^4$ is the attachment point to the linker (L), then $R^3$ is selected from H, halo, $CF_3$.

12. The ocular lens according to claim 10, wherein the UV absorbing moiety (U) has a structure of formula (V):

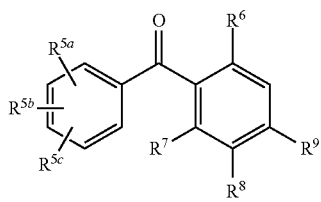

(V)

wherein
$R^{5a}$, $R^{5b}$ and $R^{5c}$ are each independently selected from the group consisting of H, halo, hydroxyl, $C_1$-$C_6$ alkyl, $C_1$-$C_6$ alkoxy, carboxylate, sulfonate, $C_6$-$C_{10}$ aryl, and substituted aryl groups;

$R^6$ and $R^7$ are each independently selected from H and OH with the proviso that $R^6$ and $R^7$ are not identical;

$R^8$ is selected from H and sulfonate; and $R^9$ is the attachment point to the linker (L).

13. The ocular lens according to claim 1, wherein the ethylenically unsaturated polymerisable moiety (Py) comprises a polymerisable functional group selected from allyl, vinyl, acryloyl, methacryloyl and styrenyl.

14. The ocular lens according to claim 1, wherein the hydrogel polymer comprises polymerised residues derived from at least two different polymerisable UV absorbers, wherein at least one of the polymerisable UV absorbers is of formula (I).

15. The ocular lens according to claim 14, wherein the hydrogel polymer comprises from about 0.1 to about 10 wt % of polymerised residues derived from the polymerisable UV absorbers, based on the total weight of monomeric units.

16. The ocular lens according to claim 1, wherein in addition to the polymerised residues derived from the polymerisable UV absorber of formula (I), the hydrogel polymer comprises polymerised residues derived from an ethylenically unsaturated monomer selected from the group consisting of acryloyl monomers, methacryloyl monomers and combinations thereof.

17. The ocular lens according to claim 1, wherein the hydrogel polymer comprises polymerised residues derived from an ethylenically unsaturated crosslinking agent.

18. The ocular lens according to claim 1, which is a contact lens or an intraocular lens.

* * * * *